US012575960B2

(12) United States Patent
Schneider et al.

(10) Patent No.: US 12,575,960 B2
(45) Date of Patent: Mar. 17, 2026

(54) URINE COLLECTION SYSTEMS HAVING ONE OR MORE OF VOLUME, PRESSURE, OR FLOW INDICATORS, AND RELATED METHODS

(71) Applicant: PureWick Corporation, El Cajon, CA (US)

(72) Inventors: Seth Schneider, Social Circle, GA (US); Claire Gloeckner, Lilburn, GA (US); Gregory Mann, Covington, GA (US); Damien Marechal, Claix (FR); Yolanda Rhodes, Cypress, TX (US)

(73) Assignee: PUREWICK CORPORATION, Covington, GA (US)

( * ) Notice: Subject to any disclaimer, the term of this patent is extended or adjusted under 35 U.S.C. 154(b) by 0 days.

(21) Appl. No.: 17/808,354

(22) Filed: Jun. 23, 2022

(65) Prior Publication Data

US 2022/0409422 A1     Dec. 29, 2022

Related U.S. Application Data

(60) Provisional application No. 63/214,570, filed on Jun. 24, 2021.

(51) Int. Cl.
   *A61F 5/451*      (2006.01)
   *A61F 5/44*       (2006.01)
(52) U.S. Cl.
   CPC ............ *A61F 5/451* (2013.01); *A61F 5/4404* (2013.01)

(58) Field of Classification Search
   CPC .......... A61F 5/451; A61F 5/4404; A61M 1/60
   See application file for complete search history.

(56) References Cited

U.S. PATENT DOCUMENTS

| | | | |
|---|---|---|---|
| 670,602 | A | 3/1901 | Baker |
| 737,443 | A | 8/1903 | Mooers |
| 1,015,905 | A | 1/1912 | Northrop |
| 1,032,841 | A | 7/1912 | Koenig |
| 1,178,644 | A | 4/1916 | Johnson |
| 1,387,726 | A | 8/1921 | Karge |
| 1,742,080 | A | 12/1929 | Jones |
| 1,979,899 | A | 11/1934 | Obrien et al. |
| 2,241,010 | A | 5/1941 | Chipley |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)

(Continued)

*Primary Examiner* — Ariana Zimbouski
*Assistant Examiner* — Matthew Wrubleski
(74) *Attorney, Agent, or Firm* — Ballard Spahr LLP

(57) ABSTRACT

Examples relate to devices, systems, and methods for fluid collection such as urine. A urine collection system includes a urine collection device configured to be positioned at least proximate to a urethra of a user, a canister having an interior region, a first conduit in fluid communication with the urine (Continued)

collection device and the canister, and one or more of a urine volume indicator, a flow indicator, and/or a pressure indicator.

30 Claims, 9 Drawing Sheets

(56) References Cited

U.S. PATENT DOCUMENTS

| | | | |
|---|---|---|---|
| 2,262,772 A | 11/1941 | Peder | |
| 2,326,881 A | 8/1943 | Packer | |
| 2,379,346 A | 6/1945 | Farrell | |
| 2,485,555 A | 10/1949 | Bester | |
| 2,571,357 A | 10/1951 | Charles | |
| 2,613,670 A | 10/1952 | Edward | |
| 2,616,426 A | 11/1952 | Adele | |
| 2,644,234 A | 7/1953 | Earl | |
| 2,648,335 A | 8/1953 | Chambers | |
| 2,859,786 A | 11/1958 | Tupper | |
| 2,944,551 A | 7/1960 | Carl | |
| 2,968,046 A | 1/1961 | Duke | |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,114,916 A | 12/1963 | Hadley | |
| 3,169,528 A | 2/1965 | Knox et al. | |
| 3,171,506 A | 3/1965 | Therkel | |
| 3,175,719 A | 3/1965 | Herndon | |
| 3,194,238 A | 7/1965 | Breece | |
| 3,198,994 A | 8/1965 | Hildebrandt et al. | |
| 3,221,742 A | 12/1965 | Egon | |
| 3,312,221 A * | 4/1967 | Overment | A61F 5/44 |
| | | | 604/350 |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,424,163 A | 1/1969 | Gravdahl | |
| 3,425,471 A | 2/1969 | Yates | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,608,552 A | 9/1971 | Broerman | |
| 3,613,123 A | 10/1971 | Langstrom | |
| 3,648,700 A | 3/1972 | Warner | |
| 3,651,810 A | 3/1972 | Ormerod | |
| 3,661,155 A | 5/1972 | Lindan | |
| 3,683,918 A | 8/1972 | Pizzella | |
| 3,699,815 A | 10/1972 | Holbrook | |
| 3,726,277 A | 4/1973 | Hirschman | |
| 3,742,952 A | 7/1973 | Magers et al. | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,865,109 A | 2/1975 | Elmore et al. | |
| 3,881,486 A | 5/1975 | Fenton | |
| 3,881,489 A | 5/1975 | Hartwell | |
| 3,915,189 A | 10/1975 | Holbrook et al. | |
| 3,931,650 A | 1/1976 | Miller | |
| 3,998,228 A | 12/1976 | Poidomani | |
| 3,999,550 A | 12/1976 | Martin | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,064,962 A | 12/1977 | Hunt | |
| 4,069,817 A | 1/1978 | Fenole et al. | |
| 4,084,589 A | 4/1978 | Kulvi | |
| 4,096,897 A | 6/1978 | Cammarata | |
| 4,116,197 A | 9/1978 | Bermingham | |
| 4,180,178 A | 12/1979 | Turner | |
| 4,187,953 A | 2/1980 | Turner | |
| 4,194,508 A | 3/1980 | Anderson | |
| 4,200,102 A | 4/1980 | Duhamel et al. | |
| 4,202,058 A | 5/1980 | Anderson | |
| 4,203,503 A | 5/1980 | Bertotti et al. | |
| 4,209,076 A | 6/1980 | Bertotti et al. | |
| 4,223,677 A | 9/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,253,542 A | 3/1981 | Ruspa et al. | |
| 4,257,418 A | 3/1981 | Hessner | |
| 4,270,539 A | 6/1981 | Frosch et al. | |
| 4,281,655 A | 8/1981 | Terauchi | |
| 4,292,916 A | 10/1981 | Bradley et al. | |
| 4,330,239 A | 5/1982 | Gannaway | |
| 4,345,341 A | 8/1982 | Saito | |
| 4,349,029 A | 9/1982 | Mott | |
| 4,352,356 A | 10/1982 | Tong | |
| 4,360,933 A | 11/1982 | Kimura et al. | |
| 4,365,363 A | 12/1982 | Windauer | |
| 4,375,841 A | 3/1983 | Vielbig | |
| 4,387,726 A | 6/1983 | Denard | |
| 4,403,991 A | 9/1983 | Hill | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt et al. | |
| 4,528,703 A | 7/1985 | Kraus | |
| 4,533,354 A | 8/1985 | Jensen et al. | |
| 4,533,357 A | 8/1985 | Hall | |
| D280,438 S | 9/1985 | Wendt | |
| 4,551,141 A | 11/1985 | Mcneil | |
| 4,553,968 A | 11/1985 | Komis | |
| 4,568,341 A | 2/1986 | Mitchell et al. | |
| 4,581,026 A | 4/1986 | Schneider | |
| 4,583,983 A | 4/1986 | Einhorn et al. | |
| 4,589,516 A | 5/1986 | Inoue et al. | |
| 4,601,716 A | 7/1986 | Smith | |
| 4,610,675 A | 9/1986 | Triunfol | |
| 4,620,333 A | 11/1986 | Ritter | |
| 4,626,250 A | 12/1986 | Schneider | |
| 4,627,846 A | 12/1986 | Ternstroem | |
| 4,631,061 A | 12/1986 | Martin | |
| 4,650,477 A | 3/1987 | Johnson | |
| 4,655,754 A * | 4/1987 | Richmond | A61M 1/60 |
| | | | 604/323 |
| 4,656,675 A | 4/1987 | Fajnsztajn | |
| 4,681,570 A | 7/1987 | Dalton | |
| 4,681,577 A | 7/1987 | Stern et al. | |
| 4,692,160 A | 9/1987 | Nussbaumer | |
| 4,707,864 A | 11/1987 | Ikematsu et al. | |
| 4,713,065 A | 12/1987 | Koot | |
| 4,713,066 A | 12/1987 | Komis | |
| 4,723,953 A | 2/1988 | Pratt et al. | |
| 4,735,841 A | 4/1988 | Sourdet | |
| 4,743,236 A | 5/1988 | Manschot | |
| 4,747,166 A | 5/1988 | Kuntz | |
| 4,752,944 A | 6/1988 | Conrads et al. | |
| 4,769,215 A | 9/1988 | Ehrenkranz | |
| 4,771,484 A | 9/1988 | Mozell | |
| 4,772,280 A | 9/1988 | Rooyakkers | |
| 4,784,654 A | 11/1988 | Beecher | |
| 4,790,830 A | 12/1988 | Hamacher | |
| 4,790,835 A | 12/1988 | Elias | |
| 4,791,686 A | 12/1988 | Taniguchi et al. | |
| 4,795,449 A | 1/1989 | Schneider et al. | |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,813,943 A | 3/1989 | Smith | |

(56)  References Cited

U.S. PATENT DOCUMENTS

| | | | |
|---|---|---|---|
| 4,820,291 A | 4/1989 | Terauchi et al. |
| 4,820,297 A | 4/1989 | Kaufman et al. |
| 4,841,728 A | 6/1989 | Jean et al. |
| 4,846,818 A | 7/1989 | Keldahl et al. |
| 4,846,819 A | 7/1989 | Welch |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-Ho |
| 4,895,140 A | 1/1990 | Bellak |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,950,262 A | 8/1990 | Takagi |
| 4,955,922 A | 9/1990 | Terauchi |
| 4,957,487 A | 9/1990 | Gerow |
| 4,965,460 A | 10/1990 | Tanaka et al. |
| 4,986,823 A | 1/1991 | Anderson et al. |
| 4,987,849 A | 1/1991 | Sherman |
| 5,002,541 A | 3/1991 | Conkling et al. |
| 5,004,463 A | 4/1991 | Nigay |
| 5,013,308 A | 5/1991 | Sullivan et al. |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | McGuire |
| 5,078,707 A | 1/1992 | Peter |
| 5,084,037 A | 1/1992 | Barnett |
| 5,100,396 A | 3/1992 | Zamierowski |
| 5,102,404 A | 4/1992 | Goldberg et al. |
| 5,112,324 A | 5/1992 | Wallace |
| 5,137,033 A | 8/1992 | Norton |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,199,444 A | 4/1993 | Wheeler |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,294,983 A | 3/1994 | Ersoz et al. |
| 5,295,979 A | 3/1994 | Delaurentis et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,457 A | 7/1994 | Cohen |
| 5,330,459 A | 7/1994 | Lavon et al. |
| 5,334,174 A | 8/1994 | Street |
| 5,340,840 A | 8/1994 | Park et al. |
| 5,382,244 A | 1/1995 | Telang |
| 5,397,315 A | 3/1995 | Schmidt et al. |
| 5,409,014 A | 4/1995 | Napoli et al. |
| 5,409,475 A | 4/1995 | Steer |
| 5,411,495 A | 5/1995 | Willingham |
| 5,423,784 A | 6/1995 | Metz |
| 5,423,788 A | 6/1995 | Rollins et al. |
| 5,437,836 A | 8/1995 | Yamada |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,593,389 A | 1/1997 | Chang |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,681,297 A | 10/1997 | Hashimoto et al. |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,735,835 A | 4/1998 | Holland |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| D409,303 S | 5/1999 | Oepping |
| 5,911,222 A | 6/1999 | Lawrence et al. |
| 5,956,782 A | 9/1999 | Olguin |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |

(56)                    References Cited

U.S. PATENT DOCUMENTS

| | | | | | | |
|---|---|---|---|---|---|---|
| 6,446,454 | B1 | 9/2002 | Lee et al. | 7,588,560 | B1 | 9/2009 | Dunlop |
| 6,467,570 | B1 | 10/2002 | Herold | 7,637,905 | B2 | 12/2009 | Saadat et al. |
| 6,475,198 | B1 | 11/2002 | Lipman et al. | 7,658,730 | B2 | 2/2010 | Conley |
| 6,479,726 | B1 | 11/2002 | Cole et al. | 7,665,359 | B2 | 2/2010 | Barber |
| 6,491,673 | B1 | 12/2002 | Palumbo et al. | 7,682,347 | B2 | 3/2010 | Parks et al. |
| 6,508,794 | B1 | 1/2003 | Palumbo et al. | 7,687,004 | B2 | 3/2010 | Allen |
| 6,524,292 | B1 | 2/2003 | Dipalma et al. | 7,695,459 | B2 | 4/2010 | Gilbert et al. |
| 6,540,729 | B1 | 4/2003 | Wada et al. | 7,695,460 | B2 | 4/2010 | Wada et al. |
| 6,547,771 | B2 | 4/2003 | Robertson et al. | 7,699,818 | B2 | 4/2010 | Gilbert |
| 6,551,293 | B1 | 4/2003 | Mitchell | 7,699,831 | B2 | 4/2010 | Bengtson et al. |
| 6,569,133 | B2 | 5/2003 | Cheng et al. | 7,722,584 | B2 | 5/2010 | Tanaka et al. |
| D476,518 | S | 7/2003 | Doppelt | 7,727,206 | B2 | 6/2010 | Gorres |
| 6,592,560 | B2 | 7/2003 | Snyder et al. | 7,740,620 | B2 | 6/2010 | Gilbert et al. |
| 6,610,038 | B1 | 8/2003 | Dipalma et al. | 7,749,205 | B2 | 7/2010 | Tazoe et al. |
| 6,618,868 | B2 | 9/2003 | Minnick | 7,755,497 | B2 | 7/2010 | Wada et al. |
| 6,620,142 | B1 | 9/2003 | Flueckiger | 7,766,887 | B2 | 8/2010 | Burns et al. |
| 6,629,651 | B1 | 10/2003 | Male et al. | 7,803,144 | B1 | 9/2010 | Vollrath |
| 6,635,037 | B1 | 10/2003 | Bennett | D625,407 | S | 10/2010 | Koizumi et al. |
| 6,635,038 | B2 | 10/2003 | Scovel | 7,806,879 | B2 | 10/2010 | Brooks et al. |
| 6,652,495 | B1 | 11/2003 | Walker | 7,811,272 | B2 | 10/2010 | Lindsay et al. |
| 6,666,850 | B1 | 12/2003 | Ahr et al. | 7,815,067 | B2 | 10/2010 | Matsumoto et al. |
| 6,685,684 | B1 | 2/2004 | Falconer | 7,833,169 | B2 | 11/2010 | Hannon |
| 6,695,828 | B1 | 2/2004 | Dipalma et al. | 7,857,806 | B2 | 12/2010 | Karpowicz et al. |
| 6,699,174 | B1 | 3/2004 | Bennett | 7,866,942 | B2 | 1/2011 | Harvie |
| 6,700,034 | B1 | 3/2004 | Lindsay et al. | 7,871,385 | B2 | 1/2011 | Levinson et al. |
| 6,702,793 | B1 | 3/2004 | Sweetser et al. | 7,875,010 | B2 | 1/2011 | Frazier et al. |
| 6,706,027 | B2 | 3/2004 | Harvie et al. | 7,901,389 | B2 | 3/2011 | Mombrinie |
| 6,732,384 | B2 | 5/2004 | Scott | 7,927,320 | B2 | 4/2011 | Goldwasser et al. |
| 6,736,977 | B1 | 5/2004 | Hall et al. | 7,927,321 | B2 | 4/2011 | Marland |
| 6,740,066 | B2 | 5/2004 | Wolff et al. | 7,931,634 | B2 | 4/2011 | Swiecicki et al. |
| 6,764,477 | B1 | 7/2004 | Chen et al. | 7,939,706 | B2 | 5/2011 | Okabe et al. |
| 6,783,519 | B2 | 8/2004 | Samuelsson | 7,946,443 | B2 | 5/2011 | Stull et al. |
| 6,796,974 | B2 | 9/2004 | Palumbo et al. | 7,947,025 | B2 | 5/2011 | Buglino et al. |
| 6,814,547 | B2 | 11/2004 | Childers et al. | 7,963,419 | B2 | 6/2011 | Burney et al. |
| 6,849,065 | B2 | 2/2005 | Schmidt et al. | 7,976,519 | B2 | 7/2011 | Bubb et al. |
| 6,857,137 | B2 | 2/2005 | Otto | 7,993,318 | B2 | 8/2011 | Olsson et al. |
| 6,885,690 | B2 | 4/2005 | Aggerstam et al. | 8,015,627 | B2 | 9/2011 | Baker et al. |
| 6,888,044 | B2 | 5/2005 | Fell et al. | 8,016,071 | B1 | 9/2011 | Martinus et al. |
| 6,893,425 | B2 | 5/2005 | Dunn et al. | 8,028,460 | B2 | 10/2011 | Williams |
| 6,912,737 | B2 | 7/2005 | Ernest et al. | 8,047,398 | B2 | 11/2011 | Dimartino et al. |
| 6,918,899 | B2 | 7/2005 | Harvie | 8,083,094 | B2 | 12/2011 | Caulfield et al. |
| 6,979,324 | B2 | 12/2005 | Bybordi et al. | 8,128,608 | B2 | 3/2012 | Thevenin |
| 7,018,366 | B2 | 3/2006 | Easter | 8,181,651 | B2 | 5/2012 | Pinel |
| 7,066,411 | B2 | 6/2006 | Male et al. | 8,181,819 | B2 | 5/2012 | Burney et al. |
| 7,122,023 | B1 | 10/2006 | Hinoki | 8,211,063 | B2 | 7/2012 | Bierman et al. |
| 7,125,399 | B2 | 10/2006 | Miskie | 8,221,369 | B2 | 7/2012 | Parks et al. |
| 7,131,964 | B2 | 11/2006 | Harvie | 8,241,262 | B2 | 8/2012 | Mahnensmith |
| 7,135,012 | B2 | 11/2006 | Harvie | 8,277,426 | B2 | 10/2012 | Wilcox et al. |
| 7,141,043 | B2 | 11/2006 | Harvie | 8,287,508 | B1 | 10/2012 | Sanchez |
| D533,972 | S | 12/2006 | La | 8,303,554 | B2 | 11/2012 | Tsai et al. |
| 7,160,273 | B2 | 1/2007 | Greter et al. | 8,322,565 | B2 | 12/2012 | Caulfield et al. |
| 7,166,092 | B2 | 1/2007 | Elson et al. | 8,337,477 | B2 | 12/2012 | Parks et al. |
| 7,171,699 | B2 | 2/2007 | Ernest et al. | D674,241 | S | 1/2013 | Bickert et al. |
| 7,171,871 | B2 | 2/2007 | Kozak | 8,343,122 | B2 | 1/2013 | Gorres |
| 7,179,951 | B2 | 2/2007 | Krishnaswamy-Mirle et al. | 8,343,125 | B2 | 1/2013 | Kawazoe et al. |
| 7,181,781 | B1 | 2/2007 | Trabold et al. | 8,353,074 | B2 | 1/2013 | Krebs |
| 7,186,245 | B1 | 3/2007 | Cheng et al. | 8,353,886 | B2 | 1/2013 | Bester et al. |
| 7,192,424 | B2 | 3/2007 | Cooper | D676,241 | S | 2/2013 | Merrill |
| 7,219,764 | B1 | 5/2007 | Forbes | 8,388,587 | B1 | 3/2013 | Gmuer et al. |
| 7,220,250 | B2 | 5/2007 | Suzuki et al. | 8,388,588 | B2 | 3/2013 | Wada et al. |
| D562,975 | S | 2/2008 | Otto | D679,807 | S | 4/2013 | Burgess et al. |
| 7,335,189 | B2 | 2/2008 | Harvie | 8,425,482 | B2 | 4/2013 | Khoubnazar |
| 7,358,282 | B2 | 4/2008 | Krueger et al. | 8,434,586 | B2 | 5/2013 | Pawelski et al. |
| 7,390,320 | B2 | 6/2008 | Machida et al. | 8,449,510 | B2 | 5/2013 | Martini et al. |
| 7,438,706 | B2 | 10/2008 | Koizumi et al. | D684,260 | S | 6/2013 | Lund et al. |
| 7,488,310 | B2 | 2/2009 | Yang | 8,470,230 | B2 | 6/2013 | Caulfield et al. |
| 7,491,194 | B1 | 2/2009 | Oliwa | 8,479,941 | B2 | 7/2013 | Matsumoto et al. |
| D591,106 | S | 4/2009 | Dominique et al. | 8,479,949 | B2 | 7/2013 | Henkel |
| 7,513,381 | B2 | 4/2009 | Heng et al. | 8,500,719 | B1 | 8/2013 | Simpson et al. |
| 7,520,872 | B2 | 4/2009 | Biggie et al. | 8,512,301 | B2 | 8/2013 | Ma |
| D593,801 | S | 6/2009 | Wilson et al. | 8,529,530 | B2 | 9/2013 | Koch et al. |
| 7,540,364 | B2 | 6/2009 | Sanderson | 8,535,284 | B2 | 9/2013 | Joder et al. |
| 7,549,511 | B2 | 6/2009 | Marocco | 8,546,639 | B2 | 10/2013 | Wada et al. |
| 7,549,512 | B2 | 6/2009 | Newberry | 8,551,062 | B2 | 10/2013 | Kay |
| 7,585,293 | B2 | 9/2009 | Vermaak | 8,551,075 | B2 | 10/2013 | Bengtson |
| | | | | 8,568,376 | B2 | 10/2013 | Delattre et al. |
| | | | | D694,404 | S | 11/2013 | Burgess et al. |
| | | | | 8,585,683 | B2 | 11/2013 | Bengtson et al. |
| | | | | 8,586,583 | B2 | 11/2013 | Hamblin et al. |

(56)         References Cited

U.S. PATENT DOCUMENTS

| | | | |
|---|---|---|---|
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,737,433 B2 | 8/2017 | Joh |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 9,968,908 B2 | 5/2018 | Ladrech et al. |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,502,198 B2 | 12/2019 | Stumpf et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 | 3/2024 | Newton |
| 11,938,053 B2 | 3/2024 | Austermann et al. |
| 11,944,740 B2 | 4/2024 | Hughett et al. |
| 11,994,122 B2 | 5/2024 | Bodain |
| 11,998,475 B2 | 6/2024 | Becker et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,090,083 B2 | 9/2024 | Ecklund et al. |
| 12,133,813 B2 | 11/2024 | Ulreich et al. |
| 12,138,195 B2 | 11/2024 | Alder et al. |
| 2001/0037097 A1 | 11/2001 | Cheng et al. |
| 2001/0037098 A1 | 11/2001 | Snyder |
| 2001/0054426 A1 | 12/2001 | Knudson et al. |
| 2002/0019614 A1 | 2/2002 | Woon |
| 2002/0026161 A1 | 2/2002 | Grundke |

(56)  References Cited

U.S. PATENT DOCUMENTS

| | | |
|---|---|---|
| 2002/0026163 A1 | 2/2002 | Grundke |
| 2002/0042945 A1 | 4/2002 | Sands |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2002/0193762 A1 | 12/2002 | Suydam |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0074724 A1 | 4/2003 | Sands |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0194792 A1 | 10/2004 | Zhuang et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0113334 A1 | 6/2006 | Mikhail et al. |
| 2006/0155214 A1 | 7/2006 | Wightman |
| 2006/0171997 A1 | 8/2006 | Gruenbacher et al. |
| 2006/0180566 A1* | 8/2006 | Mataya ................ A61J 1/1425 |
| | | 215/230 |
| 2006/0200102 A1 | 9/2006 | Cooper |
| 2006/0229575 A1* | 10/2006 | Boiarski ............... G01F 23/242 |
| | | 604/318 |
| 2006/0229576 A1 | 10/2006 | Conway et al. |
| 2006/0231648 A1 | 10/2006 | Male et al. |
| 2006/0235266 A1 | 10/2006 | Nar |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1* | 1/2007 | Karpowicz ............. A61M 1/80 |
| | | 604/326 |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1* | 1/2008 | Tanaka ................... A61F 5/451 |
| | | 604/326 |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Mrginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1 | 1/2010 | Thevenin |
| 2010/0031429 A1 | 2/2010 | Kim et al. |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1* | 2/2011 | Johannison ............. A61M 1/60 |
| | | 604/319 |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |

(56)                    References Cited

U.S. PATENT DOCUMENTS

| | | |
|---|---|---|
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1* | 6/2013 | Gordon .............. A61M 1/984 |
| | | 604/319 |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1 | 4/2017 | Hinayama et al. |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |

(56)　　　　References Cited

U.S. PATENT DOCUMENTS

| | | |
|---|---|---|
| 2019/0133126 A1 | 5/2019 | Modak et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1* | 10/2019 | McMenamin .... A61M 25/0017 |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Mllarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2022/0409422 A1 | 12/2022 | Schneider et al. |
| 2023/0018845 A1 | 1/2023 | Lee |

(56) References Cited

U.S. PATENT DOCUMENTS

| | | |
|---|---|---|
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Mn et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277360 A1 | 9/2023 | Lambert et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065874 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |
| 2024/0148539 A1 | 5/2024 | Austermann et al. |
| 2024/0261131 A1 | 8/2024 | Garvey et al. |
| 2025/0009552 A1 | 1/2025 | Blabas et al. |
| 2025/0073055 A1 | 3/2025 | Ecklund et al. |

FOREIGN PATENT DOCUMENTS

| | | |
|---|---|---|
| AU | 2022349367 A1 | 4/2024 |
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 205924282 U | 2/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 111991136 A | 11/2020 |
| CN | 112022488 A | 12/2020 |
| CN | 212234893 U | 12/2020 |
| CN | 212466312 U | 2/2021 |
| CN | 112566550 A | 3/2021 |
| CN | 112603184 A | 4/2021 |
| CN | 213490035 U | 6/2021 |
| CN | 114007493 A | 2/2022 |
| CN | 114375187 A | 4/2022 |
| CN | 116096332 A | 5/2023 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 102012112818 A1 | 6/2014 |
| DE | 202015104597 U1 | 7/2016 |
| DE | 102020121462 B3 | 1/2022 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1658831 B1 | 1/2008 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3569205 B1 | 6/2023 |
| EP | 4382082 A2 | 6/2024 |

(56)                    References Cited

FOREIGN PATENT DOCUMENTS

| | | | |
|---|---|---|---|
| EP | 4445881 | A2 | 10/2024 |
| EP | 4464288 | A2 | 11/2024 |
| EP | 4527361 | A2 | 3/2025 |
| GB | 871820 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 2017070400 | A | 4/2017 |
| JP | 2017512603 | A | 5/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020520775 | A | 7/2020 |
| JP | 2021007472 | A | 1/2021 |
| JP | 2021120686 | A | 8/2021 |
| JP | 2021522009 | A | 8/2021 |
| JP | 2021522013 | A | 8/2021 |
| JP | 7129493 | B2 | 8/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090104426 | A | 10/2009 |
| KR | 20090110359 | A | 10/2009 |
| KR | 20120005922 | A | 1/2012 |
| KR | 20140039485 | A | 4/2014 |
| KR | 101432639 | B1 | 8/2014 |
| KR | 20180106659 | A | 10/2018 |
| KR | 20180108774 | A | 10/2018 |
| PT | 2068717 | E | 6/2013 |
| SE | 505542 | C2 | 9/1997 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | WO-0079497 | A1 * | 12/2000 | ............. A61F 13/42 |
| WO | 0145618 | A1 | 6/2001 |

(56)                    References Cited

FOREIGN PATENT DOCUMENTS

| | | | |
|---|---|---|---|
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |

(56) References Cited

FOREIGN PATENT DOCUMENTS

| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022029662 A1 | 2/2022 |
| WO | 2022031943 A1 | 2/2022 |
| WO | 2022035745 A1 | 2/2022 |
| WO | 2022051220 A1 | 3/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023023777 A1 | 3/2023 |
| WO | 2023034139 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024043871 A1 | 2/2024 |
| WO | 2024058788 A1 | 3/2024 |
| WO | 2024253655 A1 | 12/2024 |
| WO | 2025034959 A1 | 2/2025 |
| WO | 2025038087 A1 | 2/2025 |
| WO | 2025038088 A1 | 2/2025 |

OTHER PUBLICATIONS

Advisory Action for U.S. Appl. No. 14/722,613 mailed Mar. 4, 2019.

Advisory Action for U.S. Appl. No. 14/952,591 mailed Jun. 1, 2018.

Advisory Action for U.S. Appl. No. 15/238,427 mailed Apr. 10, 2019.

Advisory Action for U.S. Appl. No. 16/899,956 mailed Jul. 9, 2021.

Advisory Action for U.S. Appl. No. 16/904,868 mailed Jul. 2, 2021.

Advisory Action for U.S. Appl. No. 16/904,868 mailed Jun. 15, 2022.

Advisory Action for U.S. Appl. No. 16/905,400 mailed Feb. 16, 2022.

Advisory Action for U.S. Appl. No. 16/905,400 mailed Jun. 9, 2021.

Corrected International Search Report and Written Opinion for International Application No. PCT/US2017/043025 mailed Jan. 11, 2018.

Corrected Notice of Allowability for U.S. Appl. No. 15/221,106 mailed Jul. 2, 2019.

Corrected Notice of Allowability for U.S. Appl. No. 15/612,325 mailed Mar. 17, 2021.

Corrected Notice of Allowability for U.S. Appl. No. 17/330,657 mailed Dec. 9, 2021.

Final Office Action for U.S. Appl. No. 14/722,613 mailed on Nov. 29, 2018.

Final Office Action for U.S. Appl. No. 14/947,759 mailed Apr. 8, 2016.

Final Office Action for U.S. Appl. No. 14/952,591 mailed Feb. 23, 2018.

Final Office Action for U.S. Appl. No. 14/952,591 mailed Nov. 1, 2019.

Final Office Action for U.S. Appl. No. 14/952,591 mailed Nov. 27, 2020.

Final Office Action for U.S. Appl. No. 15/171,968 mailed Feb. 14, 2020.

Final Office Action for U.S. Appl. No. 15/171,968 mailed Mar. 19, 2019.

Final Office Action for U.S. Appl. No. 15/221,106 mailed Jan. 23, 2019.

Final Office Action for U.S. Appl. No. 15/238,427 mailed Jan. 2, 2019.

Final Office Action for U.S. Appl. No. 15/260,103 mailed Feb. 14, 2019.

Final Office Action for U.S. Appl. No. 15/612,325 mailed Sep. 17, 2020.

Final Office Action for U.S. Appl. No. 16/452,145 mailed Mar. 25, 2022.

Final Office Action for U.S. Appl. No. 16/478,180 mailed Jun. 22, 2022.

Final Office Action for U.S. Appl. No. 16/899,956 mailed Apr. 19, 2021.

Final Office Action for U.S. Appl. No. 16/904,868 mailed Mar. 10, 2022.

Final Office Action for U.S. Appl. No. 16/904,868 mailed Mar. 26, 2021.

Final Office Action for U.S. Appl. No. 16/905,400 mailed Apr. 6, 2021.

Final Office Action for U.S. Appl. No. 16/905,400 mailed Dec. 9, 2021.

Final Office Action for U.S. Appl. No. 17/088,272 mailed May 25, 2021.

Final Office Action for U.S. Appl. No. 29/624,661 mailed Feb. 18, 2020.

International Search Report and Written Opinion from International Application No. PCT/US2016/049274 mailed Dec. 1, 2016.

(56) References Cited

OTHER PUBLICATIONS

International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/012794 mailed May 3, 2022.
International Search Report and Written Opinion from International Application No. PCT/US2022/015471 mailed May 16, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Application No. 15/260, 103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 17/088,272 mailed Jun. 15, 2022.
Issue Notification for U.S. Appl. No. 29/624,661 mailed Aug. 4, 2021.
Non-Final Office Action for U.S. Appl. No. 14/592,591 mailed Mar. 20, 2020.

(56)     References Cited

OTHER PUBLICATIONS

Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.

Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Apr. 19, 2022.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/384,196, filed Dec. 19, 2016.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.

(56)         References Cited

OTHER PUBLICATIONS

U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914 filed May 25, 222.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.

(56)                    References Cited

OTHER PUBLICATIONS

U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
BOEHRINGER CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.

"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.

(56)  References Cited

OTHER PUBLICATIONS

Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl, No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.

Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/IB2021/057173 mailed Nov. 5, 2021.
International Search Report and Written Opinion from International Application No. PCT/US2022/014285 mailed Sep. 28, 2022.

(56)  References Cited

OTHER PUBLICATIONS

International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015781 mailed May 6, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.

Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed May 3, 2023.

(56)　　　　References Cited

OTHER PUBLICATIONS

Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Dec. 1, 2022.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 17/451,719, filed Oct. 19, 2021.
U.S. Appl. No. 17/664,487, filed May 23, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.

(56)                    References Cited

OTHER PUBLICATIONS

U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 63/150,640, filed Feb. 18, 2021.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas,"A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article,"Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 17/444,792 mailed Jul. 8, 2024.
Advisory Action for U.S. Appl. No. 17/451,345 mailed Jul. 3, 2024.
Advisory Action for U.S. Appl. No. 17/645,821 mailed Jul. 2, 2024.
Final Office Action for U.S. Appl. No. 17/051,585 mailed Jul. 5, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Non-Final Office Action for U.S. Appl. No. 17/378,015 mailed Jul. 5, 2024.
Non-Final Office Action for U.S. Appl. No. 17/663,330 mailed Jul. 1, 2024.
Non-Final Office Action for U.S. Appl. No. 18/451,080 mailed Jul. 30, 2024.
Notice of Allowance for U.S. Appl. No. 16/452,145 mailed Jul. 11, 2024.
Notice of Allowance for U.S. Appl. No. 17/447,123 mailed Jul. 26, 2024.
Notice of Allowance for U.S. Appl. No. 17/501,591 mailed Jul. 31, 2024.
Notice of Allowance for U.S. Appl. No. 17/664,914 mailed Jul. 26, 2024.
Notice of Allowance for U.S. Appl. No. 18/198,464 mailed Jul. 30, 2024.
U.S. Appl. No. 18/728,604, filed Jul. 12, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
Advisory Action for U.S. Appl. No. 17/051,585 mailed Oct. 8, 2024.
Advisory Action for U.S. Appl. No. 17/653,920 mailed Oct. 28, 2024.
Advisory Action for U.S. Appl. No. 18/134,857 mailed Oct. 23, 2024.
Corrected Notice of Allowability for U.S. Appl. No. 17/450,864 mailed Oct. 24, 2024.
Final Office Action for U.S. Appl. No. 17/451,354 mailed Oct. 28, 2024.
Final Office Action for U.S. Appl. No. 17/597,673 mailed Oct. 22, 2024.
Final Office Action for U.S. Appl. No. 18/003,029 mailed Oct. 22, 2024.
Final Office Action for U.S. Appl. No. 18/164,800 mailed Oct. 22, 2024.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 17/662,700 mailed Oct. 23, 2024.
Non-Final Office Action for U.S. Appl. No. 17/444,792 mailed Oct. 30, 2024.
Non-Final Office Action for U.S. Appl. No. 17/625,941 mailed Nov. 4, 2024.
Non-Final Office Action for U.S. Appl. No. 17/757,311 mailed Oct. 22, 2024.
Notice of Allowance for U.S. Appl. No. 17/661,090 mailed Oct. 30, 2024.
Notice of Allowance for U.S. Appl. No. 18/140,751 mailed Nov. 1, 2024.
Restriction Requirement for U.S. Appl. No. 17/756,201 mailed Oct. 4, 2024.
Restriction Requirement for U.S. Appl. No. 17/758,152 mailed Nov. 5, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 63/711,438, filed Oct. 24, 2024.
U.S. Appl. No. 63/711,445, filed Oct. 24, 2024.
"Dictionary.com, ABUT Definition and Meaning", Dictionary.com, https://www.dictionary.com/browse/abut, 2024, 1 page.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/646,771 mailed Feb. 29, 2024.
Advisory Action for U.S. Appl. No. 17/664,487 mailed Mar. 13, 2024.
Advisory Action for U.S. Appl. No. 18/139,523 mailed Apr. 24, 2024.
Advisory Action for U.S. Appl. No. 18/140,163 mailed Jun. 3, 2024.

(56)          References Cited

OTHER PUBLICATIONS

Advisory Action for U.S. Appl. No. 18/140,751 mailed Apr. 24, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/657,474 mailed Jun. 19, 2024.
Non-Final Office Action for U.S. Appl. No. 16/369,676 mailed Feb. 29, 2024.
Non-Final Office Action for U.S. Appl. No. 16/452,258 mailed Jun. 20, 2024.
Non-Final Office Action for U.S. Appl. No. 16/904,868 mailed Mar. 12, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/664,487 mailed Jun. 17, 2024.
Non-Final Office Action for U.S. Appl. No. 18/003,029 mailed Mar. 26, 2024.

Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 17/326,980 mailed Apr. 5, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/527,769 mailed Jun. 17, 2024.
Restriction Requirement for U.S. Appl. No. 17/667,097 mailed Mar. 20, 2024.
U.S. Appl. No. 17/444,792, filed Aug. 10, 2021.
U.S. Appl. No. 18/249,577, filed Oct. 19, 2021.
U.S. Appl. No. 18/610,523, filed Mar. 20, 2024.
U.S. Appl. No. 18/662,216, filed May 13, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/757,964, filed Jun. 28, 2024.
U.S. Appl. No. 18/758,025, filed Jun. 28, 2024.
U.S. Appl. No. 63/561,893, filed Dec. 11, 2023.
"OBLONG", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Corrected Notice of Allowability for U.S. Appl. No. 17/501,591 mailed Aug. 9, 2024.
Corrected Notice of Allowability for U.S. Appl. No. 17/664,914 mailed Aug. 9, 2024.
Final Office Action for U.S. Appl. No. 17/446,256 mailed Aug. 7, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 18/134,857 mailed Jul. 25, 2024.
International Search Report and Written Opinion from International Application No. PCT/US2023/036238 mailed Jul. 22, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.

(56)         References Cited

OTHER PUBLICATIONS

Issue Notification for U.S. Appl. No. 17/453,560 mailed Aug. 7, 2024.
Non-Final Office Action for U.S. Appl. No. 16/478,180 mailed Aug. 7, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/653,314 mailed Aug. 29, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 18/139,523 mailed Aug. 26, 2024.
Non-Final Office Action for U.S. Appl. No. 18/426,795 mailed Aug. 9, 2024.
Notice of Allowance for U.S. Appl. No. 17/667,067 mailed Aug. 28, 2024.
Notice of Allowance for U.S. Appl. No. 18/140,163 mailed Aug. 21, 2024.
Notice of Allowance for U.S. Appl. No. 18/389,009 mailed Aug. 28, 2024.
Restriction Requirement for U.S. Appl. No. 17/625,941 mailed Aug. 7, 2024.
U.S. Appl. No. 17/013,822, filed Sep. 7, 2020.
U.S. Appl. No. 18/836,204, filed Aug. 6, 2024.
U.S. Appl. No. 18/841,630, filed Aug. 26, 2024.
U.S. Appl. No. 63/568,615, filed Mar. 22, 2024.
U.S. Appl. No. 63/683,428, filed Aug. 15, 2024.
Final Office Action for U.S. Appl. No. 16/433,773 mailed Sep. 9, 2024.
International Search Report and Written Opinion from International Application No. PCT/US2023/085516 mailed Aug. 26, 2024.
Non-Final Office Action for U.S. Appl. No. 17/614,173 mailed Sep. 24, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 18/584,002 mailed Sep. 19, 2024.
Notice of Allowance for U.S. Appl. No. 16/904,868 mailed Sep. 29, 2024.
Notice of Allowance for U.S. Appl. No. 17/179,116 mailed Sep. 13, 2024.
Notice of Allowance for U.S. Appl. No. 17/450,864 mailed Sep. 18, 2024.
Restriction Requirement for U.S. Appl. No. 17/596,629 mailed Sep. 19, 2024.
Restriction Requirement for U.S. Appl. No. 17/878,268 mailed Sep. 20, 2024.
U.S. Appl. No. 18/828,559, filed Sep. 9, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
Advisory Action for U.S. Appl. No. 17/446,256 mailed Nov. 19, 2024.
Advisory Action for U.S. Appl. No. 17/653,137 mailed Nov. 20, 2024.
Corrected Notice of Allowability for U.S. Appl. No. 18/426,795 mailed Dec. 4, 2024.
Final Office Action for U.S. Appl. No. 17/655,464 mailed Nov. 29, 2024.
Issue Notification for U.S. Appl. No. 17/447,123 mailed Nov. 13, 2024.
Issue Notification for U.S. Appl. No. 17/664,914 mailed Nov. 6, 2024.

Issue Notification for U.S. Appl. No. 18/140,163 mailed Dec. 4, 2024.
Issue Notification for U.S. Appl. No. 18/198,464 mailed Nov. 20, 2024.
Non-Final Office Action for U.S. Appl. No. 17/653,920 mailed Nov. 27, 2024.
Non-Final Office Action for U.S. Appl. No. 17/759,697 mailed Dec. 4, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/663,330 mailed Nov. 20, 2024.
Notice of Allowance for U.S. Appl. No. 18/426,795 mailed Nov. 20, 2024.
Restriction Requirement for U.S. Appl. No. 17/754,736 mailed Nov. 20, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 63/720,004, filed Nov. 13, 2024.
Advisory Action for U.S. Appl. No. 17/446,654 mailed Feb. 28, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 18/003,029 mailed Jan. 8, 2025.
Advisory Action for U.S. Appl. No. 18/164,800 mailed Jan. 8, 2025.
Corrected Notice of Allowability for U.S. Appl. No. 17/646,771 mailed Jan. 17, 2025.
Corrected Notice of Allowability for U.S. Appl. No. 18/134,857 mailed Mar. 14, 2025.
Final Office Action for U.S. Appl. No. 16/452,258 mailed Jan. 6, 2025.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/625,941 mailed Feb. 18, 2025.
Final Office Action for U.S. Appl. No. 17/653,314 mailed Jan. 30, 2025.
Final Office Action for U.S. Appl. No. 17/664,487 mailed Jan. 13, 2025.
Final Office Action for U.S. Appl. No. 17/757,311 mailed Mar. 31, 2025.
International Search Report and Written Opinion from International Application No. PCT/US2023/031432 mailed Feb. 29, 2024.
International Search Report and Written Opinion from International Application No. PCT/US2024/053681 mailed Jan. 27, 2025.
Issue Notification for U.S. Appl. No. 16/478,180 mailed Mar. 5, 2025.
Issue Notification for U.S. Appl. No. 17/051,585 mailed Mar. 26, 2025.
Issue Notification for U.S. Appl. No. 17/179,116 mailed Dec. 25, 2024.
Issue Notification for U.S. Appl. No. 17/450,864 mailed Jan. 8, 2025.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/646,771 mailed Mar. 19, 2025.

(56)　　　　　References Cited

OTHER PUBLICATIONS

Issue Notification for U.S. Appl. No. 17/661,090 mailed Feb. 5, 2025.

Issue Notification for U.S. Appl. No. 17/663,330 mailed Feb. 26, 2025.

Issue Notification for U.S. Appl. No. 17/667,097 mailed Dec. 11, 2024.

Issue Notification for U.S. Appl. No. 18/140,751 mailed Feb. 12, 2025.

Issue Notification for U.S. Appl. No. 18/389,009 mailed Dec. 18, 2024.

Issue Notification for U.S. Appl. No. 18/426,795 mailed Feb. 19, 2025.

Non-Final Office Action for U.S. Appl. No. 16/433,773 mailed Feb. 28, 2025.

Non-Final Office Action for U.S. Appl. No. 17/051,600 mailed Feb. 28, 2025.

Non-Final Office Action for U.S. Appl. No. 17/394,055 mailed Mar. 13, 2025.

Non-Final Office Action for U.S. Appl. No. 17/394,055 mailed Mar. 19, 2025.

Non-Final Office Action for U.S. Appl. No. 17/446,256 mailed Dec. 13, 2024.

Non-Final Office Action for U.S. Appl. No. 17/451,354 mailed Mar. 19, 2025.

Non-Final Office Action for U.S. Appl. No. 17/631,619 mailed Mar. 19, 2025.

Non-Final Office Action for U.S. Appl. No. 17/645,821 mailed Mar. 31, 2025.

Non-Final Office Action for U.S. Appl. No. 17/653,137 mailed Jan. 28, 2025.

Non-Final Office Action for U.S. Appl. No. 17/655,464 mailed Mar. 20, 2025.

Non-Final Office Action for U.S. Appl. No. 17/754,736 mailed Mar. 31, 2025.

Non-Final Office Action for U.S. Appl. No. 17/758,152 mailed Apr. 8, 2025.

Non-Final Office Action for U.S. Appl. No. 17/809,083 mailed Apr. 2, 2025.

Non-Final Office Action for U.S. Appl. No. 17/809,083 mailed Mar. 7, 2025.

Non-Final Office Action for U.S. Appl. No. 17/878,268 mailed Mar. 17, 2025.

Non-Final Office Action for U.S. Appl. No. 17/907,125 mailed Dec. 13, 2024.

Non-Final Office Action for U.S. Appl. No. 17/996,064 mailed Mar. 6, 2025.

Notice of Allowance for U.S. Appl. No. 16/478,180 mailed Dec. 16, 2024.

Notice of Allowance for U.S. Appl. No. 16/904,868 mailed Jan. 21, 2025.

Notice of Allowance for U.S. Appl. No. 17/051,585 mailed Dec. 26, 2024.

Notice of Allowance for U.S. Appl. No. 17/444,792 mailed Mar. 28, 2025.

Notice of Allowance for U.S. Appl. No. 17/596,629 mailed Jan. 29, 2025.

Notice of Allowance for U.S. Appl. No. 17/597,673 mailed Feb. 26, 2025.

Notice of Allowance for U.S. Appl. No. 17/646,771 mailed Dec. 17, 2024.

Notice of Allowance for U.S. Appl. No. 17/749,340 mailed Feb. 14, 2025.

Notice of Allowance for U.S. Appl. No. 17/758,316 mailed Mar. 24, 2025.

Notice of Allowance for U.S. Appl. No. 17/996,155 mailed Mar. 11, 2025.

Notice of Allowance for U.S. Appl. No. 18/134,857 mailed Feb. 20, 2025.

Notice of Allowance for U.S. Appl. No. 18/415,080 mailed Dec. 30, 2024.

Notice of Allowance for U.S. Appl. No. 18/584,002 mailed Jan. 8, 2025.

Restriction Requirement for U.S. Appl. No. 17/809,083 mailed Dec. 31, 2024.

Restriction Requirement for U.S. Appl. No. 17/929,887 mailed Mar. 10, 2025.

U.S. Appl. No. 18/982,930, filed Dec. 16, 2024.

U.S. Appl. No. 19/038,774, filed Jan. 28, 2025.

U.S. Appl. No. 19/039,165, filed Jan. 28, 2025.

U.S. Appl. No. 19/046,047, filed Feb. 5, 2025.

U.S. Appl. No. 19/047,728, filed Feb. 7, 2025.

U.S. Appl. No. 19/048,004, filed Feb. 7, 2025.

U.S. Appl. No. 19/049,501, filed Feb. 10, 2025.

U.S. Appl. No. 19/049,783, filed Feb. 10, 2025.

U.S. Appl. No. 19/058,726, filed Feb. 20, 2025.

U.S. Appl. No. 19/069,480, filed Mar. 4, 2025.

U.S. Appl. No. 19/078,602, filed Mar. 13, 2025.

U.S. Appl. No. 19/092,262, filed Mar. 27, 2025.

U.S. Appl. No. 19/103,165, filed Feb. 11, 2025.

U.S. Appl. No. 19/110,938, filed Mar. 12, 2025.

U.S. Appl. No. 19/111,921, filed Mar. 14, 2025.

U.S. Appl. No. 19/171,983, filed Apr. 7, 2025.

U.S. Appl. No. 63/181,709, filed Apr. 29, 2021.

U.S. Appl. No. 63/564,696, filed Mar. 13, 2024.

Foamtech, "Foam Packaging Isnert: Best Selection Guide", https://web/archive.org/web/20170922162235/http://www.foamtechchina/com:80/foam-packaging-insert/, Sep. 22, 2017, 25 pages.

Advisory Action for U.S. Appl. No. 16/478,180 mailed Sep. 21, 2022.

Final Office Action for U.S. Appl. No. 16/449,039 mailed Aug. 1, 2022.

Final Office Action for U.S. Appl. No. 16/452,258 mailed Jun. 14, 2022.

International Search Report and Written Opinion from International Application No. PCT/US2021/039866 mailed Oct. 7, 2021.

International Search Report and Written Opinion from International Application No. PCT/US2021/055515 mailed Jan. 28, 2022.

International Search Report and Written Opinion from International Application No. PCT/US2022/011421 mailed Jun. 13, 2022.

International Search Report and Written Opinion from International Application No. PCT/US2022/015492 mailed Apr. 26, 2022.

International Search Report and Written Opinion from International Application No. PCT/US2022/019480 mailed Jun. 13, 2022.

International Search Report and Written Opinion from International Application No. PCT/US2022/021103 mailed Jun. 23, 2022.

Issue Notification for U.S. Appl. No. 17/330,657 mailed Jun. 22, 2022.

Non-Final Office Action for U.S. Appl. No. 17/662,700 mailed Jul. 22, 2022.

Notice of Allowance for U.S. Appl. No. 16/899,956 mailed Aug. 10, 2022.

Notice of Allowance for U.S. Appl. No. 16/905,400 mailed Aug. 17, 2022.

U.S. Appl. No. 17/758,152, filed Jun. 29, 2022.

U.S. Appl. No. 17/758,316, filed Jul. 1, 2022.

U.S. Appl. No. 17/759,697, filed Jul. 28, 2022.

U.S. Appl. No. 17/878,268, filed Aug. 1, 2022.

U.S. Appl. No. 17/907,125, filed Sep. 23, 2022.

U.S. Appl. No. 17/912,147, filed Sep. 16, 2022.

U.S. Appl. No. 17/929,887, filed Sep. 6, 2022.

U.S. Appl. No. 17/930,238, filed Sep. 7, 2022.

U.S. Appl. No. 17/933,590, filed Sep. 20, 2022.

U.S. Appl. No. 62/967,158, filed Jan. 26, 2020.

U.S. Appl. No. 62/991,754, filed Mar. 19, 2020.

U.S. Appl. No. 63/241,328, filed Sep. 7, 2021.

* cited by examiner

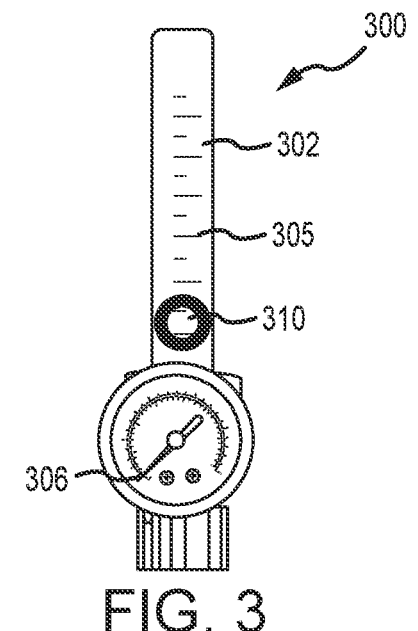
FIG. 3
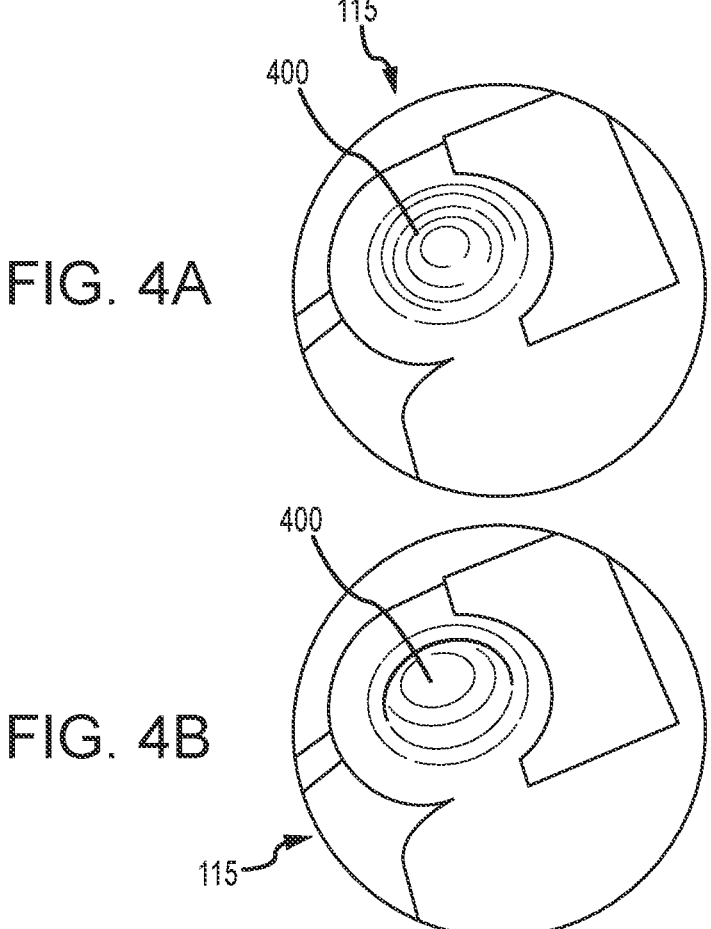
FIG. 4A
FIG. 4B

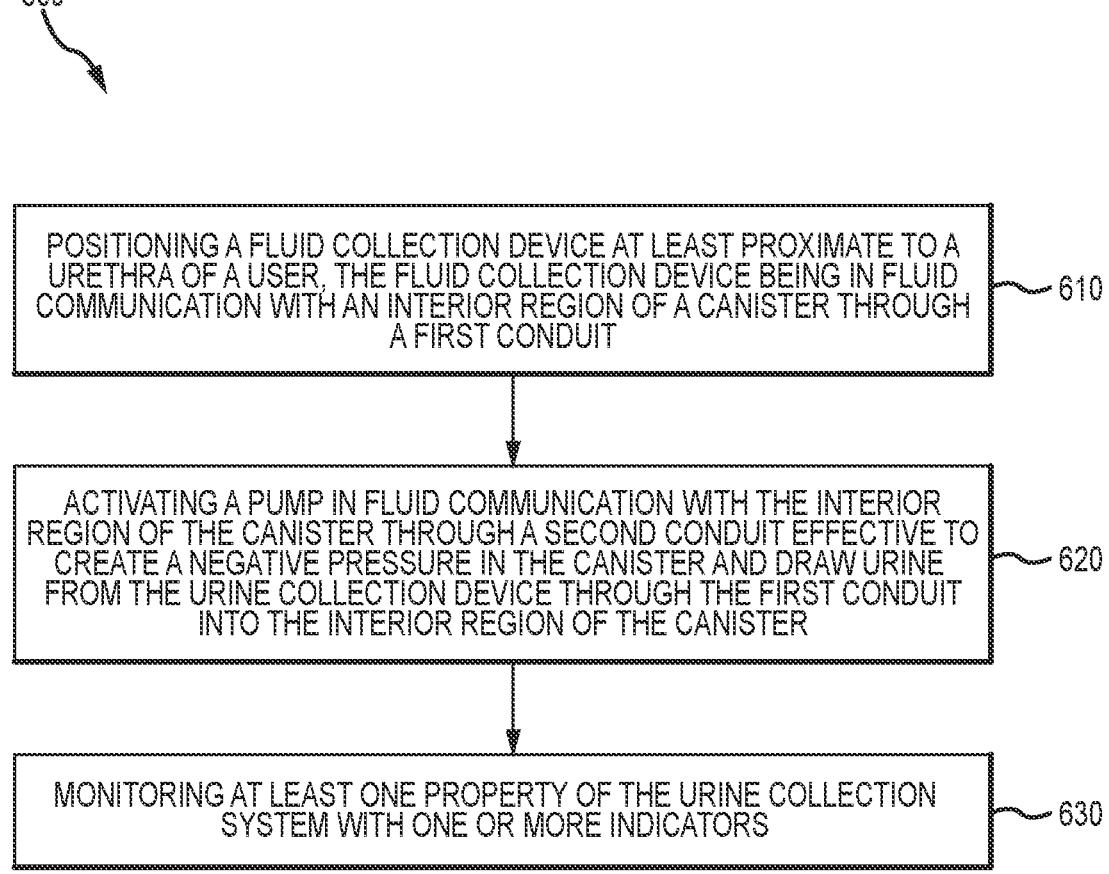

600

POSITIONING A FLUID COLLECTION DEVICE AT LEAST PROXIMATE TO A URETHRA OF A USER, THE FLUID COLLECTION DEVICE BEING IN FLUID COMMUNICATION WITH AN INTERIOR REGION OF A CANISTER THROUGH A FIRST CONDUIT — 610

ACTIVATING A PUMP IN FLUID COMMUNICATION WITH THE INTERIOR REGION OF THE CANISTER THROUGH A SECOND CONDUIT EFFECTIVE TO CREATE A NEGATIVE PRESSURE IN THE CANISTER AND DRAW URINE FROM THE URINE COLLECTION DEVICE THROUGH THE FIRST CONDUIT INTO THE INTERIOR REGION OF THE CANISTER — 620

MONITORING AT LEAST ONE PROPERTY OF THE URINE COLLECTION SYSTEM WITH ONE OR MORE INDICATORS — 630

FIG. 6

URINE COLLECTION SYSTEMS HAVING ONE OR MORE OF VOLUME, PRESSURE, OR FLOW INDICATORS, AND RELATED METHODS

CROSS-REFERENCE TO RELATED APPLICATIONS

This application claims priority to U.S. Provisional Patent Application No. 63/214,570 filed on Jun. 24, 2021, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections. Conventional urine collection devices also may be limited to use when a patient is confined to a bed in a supine position.

Thus, users and manufacturers of fluid collection devices continue to seek new and improved devices, systems, and methods to collect urine.

SUMMARY

Embodiments disclosed herein are related to urine collection systems having volume, pressure, and/or flow indicators, and related methods. In an embodiment, a urine collection system includes a urine collection device configured to be positioned at least proximate to a urethra of a user, a canister having an interior region, a first conduit in fluid communication with the urine collection device and the canister, and one or more indicators configured to detect at least one property of the urine collection system. The one or more indicators may include at least a urine volume indicator secured to the canister and configured to detect a property relating at least to a volume of urine in the canister. The one or more indicators may include at least a flow indicator positioned to detect a property relating at least to a flow of fluid through the first conduit between the canister and the urine collection device. The one or more indicators may include at least a pressure indicator secured to the canister and configured to detect a property relating at least to a pressure in the interior region of the canister.

In an embodiment, a method of collecting urine from a user includes positioning a fluid collection device at least proximate to a urethra of a user, the fluid collection device being in fluid communication with an interior region of a canister through a first conduit. The method also includes activating a pump in fluid communication with the interior region of the canister through a second conduit effective to create a negative pressure in the canister and draw urine from the urine collection device through the first conduit into the interior region of the canister. The method also includes monitoring at least one property of the urine collection system with one or more indicators. The one or more properties may include at least a property relating at least to a volume of urine in the canister with a urine volume indicator secured to the canister. The one or more properties may include at least a property relating at least to a flow of fluid through the first conduit with a flow indicator in fluid communication with the first conduit and positioned between the canister and the urine collection device. The one or more properties may include at least a property relating at least to a pressure in the interior region of the canister with a pressure indicator secured to the canister.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 3 is a side view of a flow indicator for a urine collection system, according to an embodiment.

FIGS. 4A and 4B are front views of a pressure indicator of FIG. 1B positioned in a urine collection container.

FIG. 6 is a flow diagram of a method of collecting fluid, according to an embodiment.

DETAILED DESCRIPTION

Embodiments disclosed herein are related to urine collection systems having one or more of volume, pressure, or flow indicators, and related methods of using the same. The devices, systems, and methods disclosed herein are configured to collect fluids from an individual. The fluids collected by the fluid collection devices may include at least one of urine, vaginal discharge, penile discharge, reproductive fluids, blood, sweat, or other bodily fluids. At least one, some, or all embodiments disclosed herein include one or more indicators that provide a user and/or caregiver with quick information about the urine collection system. The indicators of at least one, some, or all embodiments described herein improve the urine collection system relative to other potential ways of assessing a condition of the urine collection system. For example, reading the volume of urine in the canister by sight must be done very close to the canister and may require glasses or corrective lenses for many users and/or caregivers. Moreover, in a conventional urine collection system, kinking of a conduit or overfilling of the canister may not be immediately evident without actual contact with the system. Technical improvements of urine collection systems described herein may include one or more of a urine volume indicator configured to detect a property relating at least to a volume of urine in a urine collection canister, a flow indicator configured to detect a property relating at least to a flow of fluid through the one or more portions of the system, or a pressure indicator configured to detect a property relating at least to a pressure in the interior region of the urine collection canister. One or more of these indicators in at least one, some, or all embodiments described herein provide low-cost ways for a user or caregiver to quickly see or assess a current condition of the system.

Figure 1A:
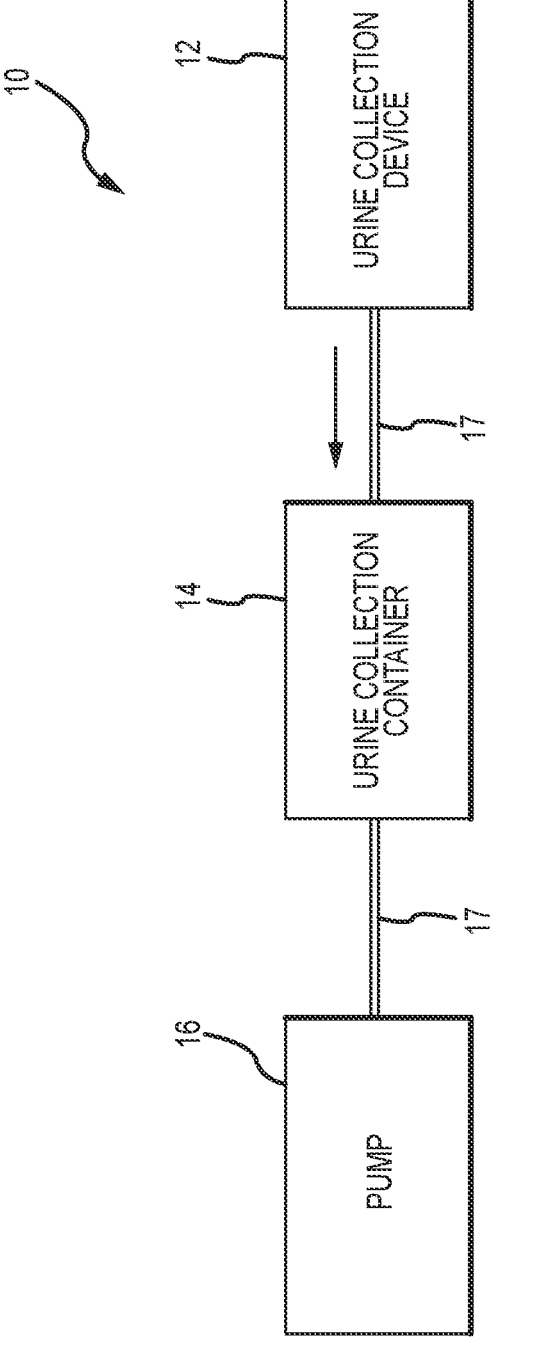
FIG. 1A is a block diagram of a portable urine collection system, according to an embodiment.

FIG. 1A is a block diagram of a fluid collection system 10, according to an embodiment. The fluid collection system 10 may be included in embodiments of fluid collection systems described herein. The system 10 includes a fluid collection device 12 (e.g., any of the fluid collection devices disclosed herein), a urine collection container 14, and a pump 16 (or vacuum source). The fluid collection device 12, the urine collection container 14, and the pump 16 may be fluidly coupled to each other via one or more conduits 17. For example, fluid collection device 12 may be operably coupled to one or more of the urine collection container 14 or the pump 16 via the conduit 17. In some embodiments, the pump 16 may be secured directly to the urine collection container 14. Fluid (e.g., urine or other bodily fluids) collected in the fluid collection device 12 may be removed from the fluid collection device 12 via the conduit 17 secured to the fluid collection device 12. Suction force may be introduced into the chamber of the fluid collection device 12 via the inlet of the conduit 17 responsive to suction (e.g., vacuum) force applied at the outlet of the conduit 17.

The suction force may be applied to the outlet of the conduit 17 by the pump 16 either directly or indirectly. The suction force may be applied indirectly via the urine collection container 14. For example, the outlet of the conduit 17 may be disposed within or fluidly coupled to an interior region of the urine collection container 14 and an additional conduit 17 may extend from the urine collection container 14 to the pump 16. Accordingly, the pump 16 may apply suction to the fluid collection device 12 via the urine collection container 14. The suction force may be applied directly via the pump 16. For example, the outlet of the conduit 17 may be disposed within the pump 16. An additional conduit 17 may extend from the pump 16 to a point outside of the fluid collection device 12, such as to the urine collection container 14. In such examples, the pump 16 may be disposed between the fluid collection device 12 and the urine collection container 14.

The urine collection container 14 is sized and shaped to retain a fluid therein. The urine collection container 14 may include a bag (e.g., drainage bag), a bottle, a canister, or a cup (e.g., collection jar), or any other enclosed container for storing bodily fluid(s) such as urine. In some examples, the conduit 17 may extend from the fluid collection device 12 and attach to the urine collection container 14 at a first point therein. An additional conduit 17 may attach to the urine collection container 14 at a second point thereon and may extend and attach to the pump 16. Accordingly, a vacuum (e.g., suction) may be drawn through fluid collection device 12 via the urine collection container 14. Fluid, such as urine, may be drained from the fluid collection device 12 using the pump 16.

The pump 16 may include one or more of a manual vacuum pump, and electric vacuum pump, a diaphragm pump, a centrifugal pump, a displacement pump, a magnetically driven pump, a peristaltic pump, or any pump configured to produce a vacuum. The pump 16 may provide a vacuum or suction to remove fluid from the fluid collection device 12. In some examples, the pump 16 may be powered by one or more of a power cord (e.g., connected to a power socket), one or more batteries, or even manual power (e.g., a hand operated vacuum pump). In some examples, the pump 16 may be sized and shaped to fit outside of, on, or within the fluid collection device 12. For example, the pump 16 may include one or more miniaturized pumps or one or more micro pumps. The vacuum sources disclosed herein may include one or more of a switch, a button, a plug, a remote, or any other device suitable to activate the pump 16.

Figure 1B:
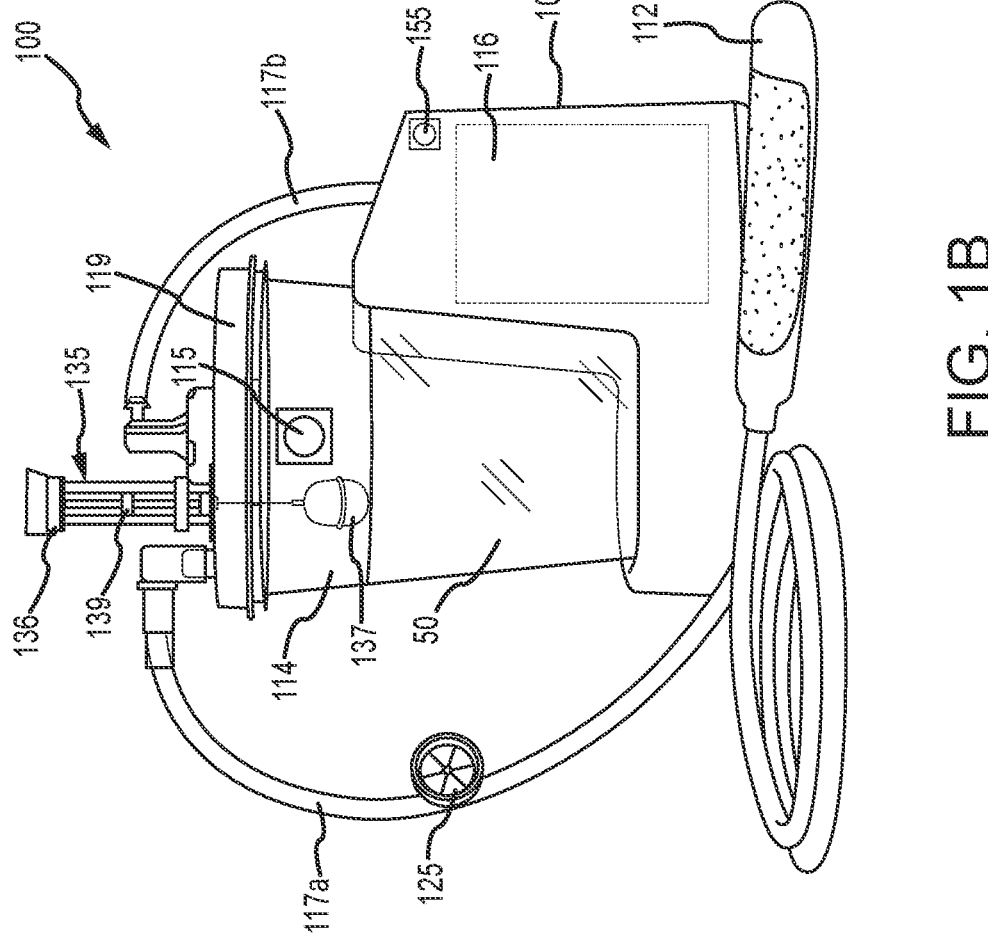
FIG. 1B is a side view of a portable urine collection system, according to an embodiment.

FIG. 1B shows an example of a urine collection system 100, according to an embodiment. The urine collection system 100 may include a urine collection device 112, a first conduit 117a in fluid communication with an interior region of the urine collection device 112, a canister 114 having an interior region in fluid communication with the internal region of the urine collection device 112 via the first conduit 117a, a second conduit 117b in fluid communication with the interior region of the canister 114, and a pump 116 (housed in a base 107 or module) in fluid communication with the interior region of the canister 114 via the second conduit 117b. The urine collection device 112 may be configured to be positioned at least proximate to a urethra of a user. While the urine collection device 112 shown in FIG. 1B includes a female urine collection device, the urine collection device 112 may instead include a male urine collection device. PCT International Application No. PCT/US2019/029616, for example, describes various embodiments of both male and female fluid collection devices, the disclosure of which are incorporated in their entirety by this reference. Moreover, the urine collection device 112 may be interchangeable in the urine collection system 100 between different types, varieties, and sizes of male or female urine collection devices. Generally, the urine collection device 112 may include a surface sized to be positioned proximate or adjacent to the urethra and configured to wick urine or other fluids away from the user. Urine or other fluids may be wicked from the surface to a reservoir in the urine collection device 112.

The urine collection system 100 also includes the first conduit 117a in fluid communication with an interior region (e.g. reservoir) of the urine collection device 112 and an interior region of the canister 114. The first conduit 117a may be positioned between the urine collection device 112 and the canister 114. The urine collection system 100 also may include the second conduit 117b providing fluid communication between the pump 116 and the interior region of the canister 114. In some embodiments, the pump 116 may be secured directly to the canister 114, and the second conduit 117b may be absent from the urine collection system 100. The conduits 117a, 117b may include a flexible tube. In some embodiments, at least a portion of the first conduit 117a is substantially opaque, thereby inhibiting viewing of the urine within the first conduit 117a.

The canister 114 may be reusable and dishwasher safe, and may include a generally rigid material such as polycarbonate or glass. In some embodiments, the canister 114 may be disposable. The urine collection system 100 may be configured to accommodate different volumetric sizes of urine collection containers 114. In some embodiments, a lid 119 having multiple ports and/or adapters for attachment of the conduits 117*a*, 117*b* thereto may be secured or securable to the canister 114. Except for the ports and/or adapters for attachment of the conduits 117*a*, 117*b*, the canister 114 may be sealed and airtight such that the urine collected in the canister 114 does not leak or spill.

The pump 116 is in fluid communication with the interior region of the canister 114 and is configured to pull a vacuum (e.g., negative pressure) on the interior region of the canister 114 effective to draw the urine from the urine collection device 112 through the first conduit 117*a* into the canister 114. The pump 116 may be secured directly to the canister 114, or the conduit 117*b* may fluidly couple the pump 116 with the interior region of the urine collection container.

The pump 116 may include one or more of a manual vacuum pump, and electric vacuum pump, a diaphragm pump, a centrifugal pump, a displacement pump, a magnetically driven pump, a peristaltic pump, or any pump configured to produce a vacuum. The pump 116 may provide a vacuum or suction to remove fluid from the fluid collection device 112. In some examples, the pump 116 may be powered by one or more batteries or other power sources. In some examples, the pump 116 may be sized and shaped to fit within a container support on a wheelchair. In some embodiments, the pump 116 may include a wall-mounted pump (shown in FIG. 2E). The pump 116 may include one or more of a switch, a button, a plug, a remote, or any other device suitable to activate the pump 116.

In some embodiments, the urine collection system 100 may include one or more (e.g., one, two, or three) of a urine volume indicator 135, a flow indicator 125, and/or a pressure indicator 115. Although the urine collection system 100 includes all three indicators of the urine volume indicator 135, the flow indicator 125, and the pressure indicator 115, some embodiments the urine collection system may include only one indicator or only any combination of two indicators of the urine volume indicator 135, the flow indicator 125, or the pressure indicator 115. In embodiments of the urine collection system 100 having two or more indicators of the urine volume indicator 135, the flow indicator 125, and the pressure indicator 115, the two or more indicators may be used simultaneously or one at a time.

With respect to the urine volume indicator 135, users and caregivers may desire to know the volume of fluid in the canister 114 and/or when the canister 114 needs to be emptied. In some embodiments, the urine volume indicator 135 is secured to the canister 114 and/or the lid 119 and is configured to detect a property relating at least to a volume of the urine 50 in the canister 114. For example, the urine volume indicator 135 may include a support member 136 secured or securable to at least one of the lid 119 or a sidewall of the canister 114. The urine volume indicator 135 may include a float member 137 configured to at least partially float on the urine 50 in the canister 114, thereby utilizing the buoyancy of the float member 137 on the urine 50 in the canister 114 to indicate or detect the property relating at least to the volume of the urine 50 in the canister 114. The float member 137 may include a hollow float member, such as a hollow ball.

In some embodiments, the urine volume indicator 135 may include one or more markers 139 configured to indicate at least a relative amount of the urine 50 in the canister 114. For example, the marker 139 may be movable on the support member 136 responsive to vertical movement of the float member 137 at least partially floating on the urine 50 in the canister 114. In some embodiments, the position of the marker 139 on the support member 136 indicates an approximate volume of the urine 50 in the canister 114. For example, when the canister 114 is substantially empty (e.g., holding substantially no urine 50), the marker 139 may be positioned at or near the bottom of the support member 136. When the canister 114 is substantially full of the urine 50, the marker 139 may be positioned at or near the top of the support member 136. In some embodiments, the support member 136 may include one or more markers indicating a percent capacity of the canister 114 being occupied by the urine 50. For example, the support member 136 may include a reference marker indicating 75% of the capacity of the canister 114 is occupied by the urine 50 when the marker 139 reaches the reference marker on the support member 136. In some embodiments, support member 136 includes one or more color reference markers. For example, the support member 136 may include (1) a green area indicating about 0% to about 50% of the capacity of the canister 114 is occupied by urine 50 when the marker 139 is positioned within the green area, (2) a yellow area indicating about 50% to about 75% of the capacity of the canister 114 is occupied by the urine 50 when the marker 139 is positioned within yellow area, and (3) a red area indicating the about 75% to about 100% of the capacity of the canister 114 is occupied by the urine 50 when the marker 139 is positioned within the red area.

In some embodiments, the urine collection system 100 includes an alert device 155 in communication with the urine volume indicator 135 and configured to produce an alert signal when the relative amount of the urine 50 in the canister 114 is at a predetermined volume. For example, the alert device 155 may be configured to produce the alert signal when the amount of the urine 50 in the canister 114 is approximately 75% or 90% of the capacity of the canister 114. The alert signal produced by the alert device 155 may include at least one of a visual (e.g., light) alert, an audible (e.g., sound) alert, or a haptic alert. In some embodiments, the urine volume indicator 135 is wired or wirelessly coupled to the pump 116 in the urine collection system 100 effective to activate (e.g., turn on) the pump 116 when the urine 50 in the canister 114 is below a predetermined volume and deactivate (e.g., turn off) the pump 116 when the urine 50 in the canister 114 is at or above a predetermined volume. The urine collection system 100 also may include a controller configured to facilitate communication between the urine volume indicator 135 and at least one (e.g., both) of the pump 116 and the urine alert device 155.

Figure 2A:
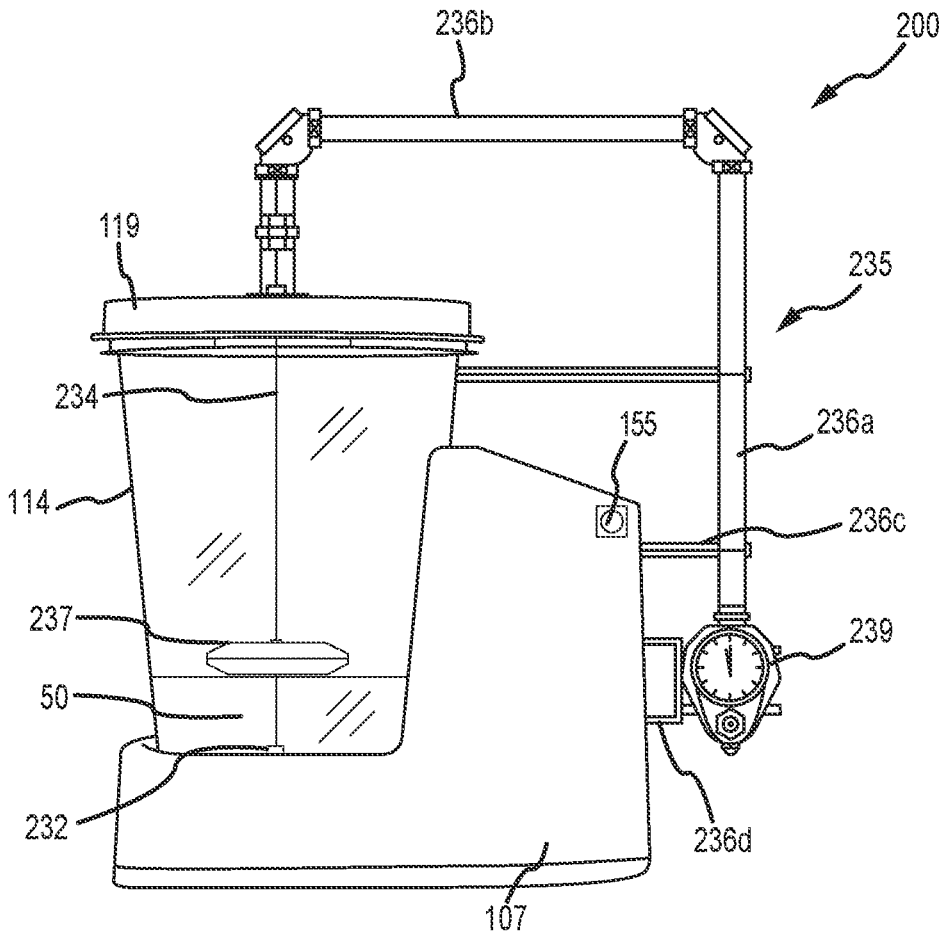
FIG. 2A is a side view of a portable urine collection system, according to an embodiment.

Turning ahead in the drawings, FIG. 2A is a side view of urine collection system 200 having a urine volume indicator 235, according to an embodiment. Unless otherwise noted, the urine collection system 200 can include any aspect of the urine collection system 100. For example, the urine collection system 200 may include one or more (e.g., all) of the pump 116, the canister 114, the lid 119, the conduits 117*a*, 117*b* (not shown), the urine collection device 112 (not shown), and/or the urine alert device 155.

The urine volume indicator 235 may be secured or securable to the canister 114 and configured to detect a property relating at least to a volume of the urine 50 in the canister 114. In some embodiments, the urine volume indicator 235 includes a float member 237 that floats on the urine 50 in the canister 114 and moves up and down along a string 234, wire, cable, or other member positioned in the interior region of the canister 114. The string 234 may extend from the lid 119 to a connector 232 secured or securable to the bottom region of the canister 114. The urine volume indicator 235 may include a gauge 239 that indicates the amount of the urine in the canister 114. For example, the gauge 239 may include numbers that display a volume or percent capacity of the canister 114 or colors that indicate relative capacity of the canister (e.g., green, yellow, and red, described above). The gauge 239 also may include a needle that moves responsive to movement of the float member 237 to one or more of the numbers or colors on the gauge to indicate the relative amount of the urine 50 in the canister 114. In some embodiments, a string, wire, or other member may extend between the float member 237 and the gauge 239 such that the needle on the gauge 239 moves responsive to up and down movement of the float member 237 in the canister 114. The urine volume indicator 235 may include one or more support members 236a, 236b, 236c, 236d configured to mount the urine volume indicator 235 to the pump 116 and/or the canister 114. The urine collection system 200 may include the urine alert device 155 configured to communicate with the urine volume indicator 235 as described above in relation to the urine volume indicator 135.

Figure 2B:
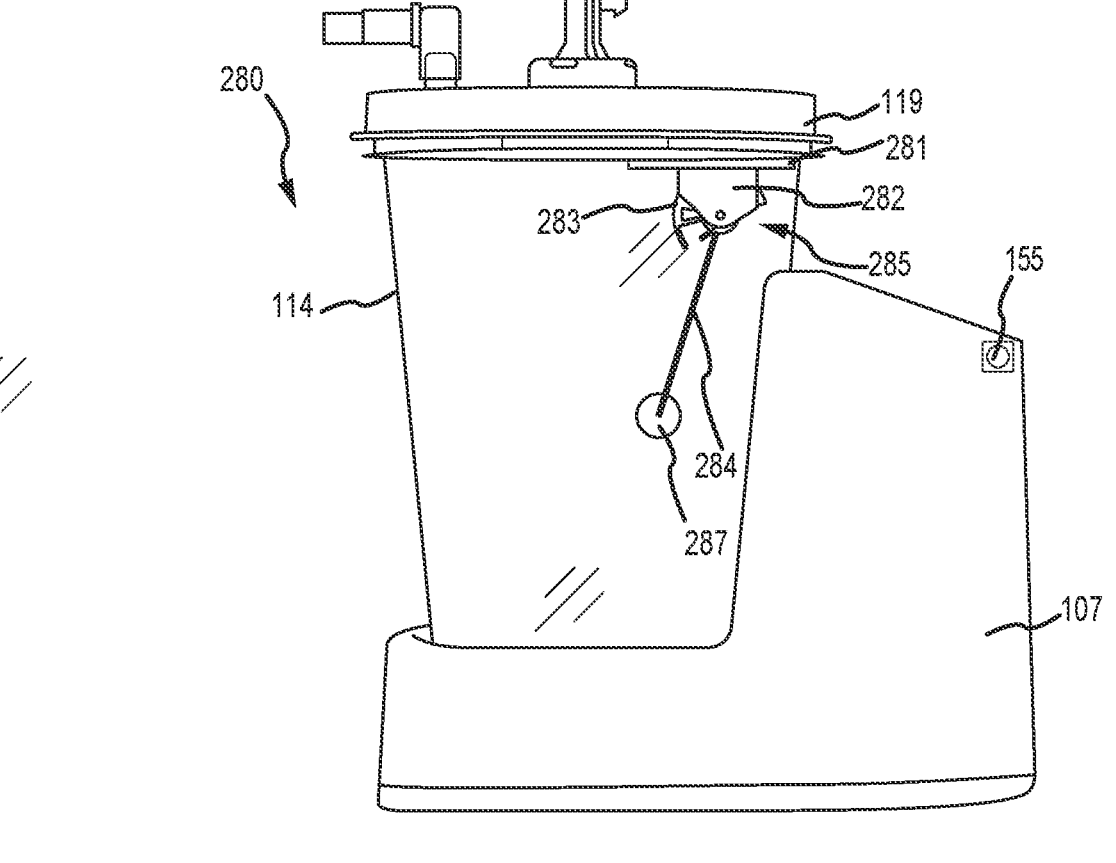
FIG. 2B is a side view of a portable urine collection system, according to an embodiment.

Turning now to FIG. 2B, a urine collection system 280 may include a urine volume indicator 285, according to an embodiment. Unless otherwise noted, the urine collection system 280 can include any aspect of the urine collection system 100. For example, the urine collection system 200 may include one or more (e.g., all) of the pump 116, the canister 114, the lid 119, the conduits 117a, 117b (not shown), the urine collection device 112 (not shown), and/or the urine alert device 155.

The urine volume indicator 285 may be secured or securable to at least one of the lid 119 or the canister 114 and configured to detect a property relating at least to a volume of the urine 50 in the canister 114. In some embodiments, the urine volume indicator 285 includes a float member 287 that floats on the urine 50 in the canister 114. A base 281 may be detachably or fixedly secured or securable to the lid 119 (shown in FIG. 2B) or a sidewall of the canister 114 (not shown), and a bracket or body 282 may extend from the base 218 into the interior region of the canister 114. A wheel 283 or dial forming at least a semi-circle may be pivotably secured to the body 282 to pivot about an axis, and an arm 284 connecting the float member 287 and the wheel 283. As the float member 287 rises with the urine in the canister 114, the portions of the wheel 283 may be exposed to indicate a numeric value of percent capacity and/or a color scale (green, yellow, and red, as described above) of percent capacity of the urine in the canister 114. In some embodiments, the urine collection system 280 may include a proximity sensor secured or securable to at least one of the lid 119 or the canister 114. The proximity sensor may include any sensor configured to detect the proximity of the float member 287 to the sensor, such as a Reed switch or a laser. The proximity sensor may generate a signal, such as an electrical signal, when the float is within a predetermined distance of the proximity sensor. The urine collection system 200 may include the urine alert device 155 configured to communicate with the urine volume indicator 235 and/or the proximity sensor as described above in relation to the urine volume indicator 135.

Figure 2C:
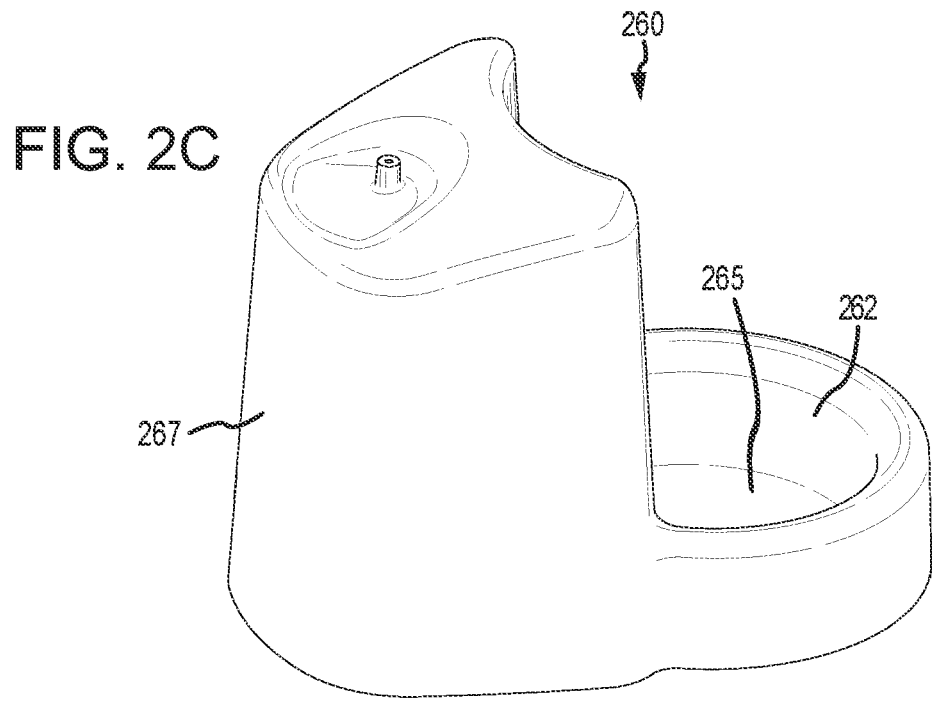
FIG. 2C is a top isometric view of a base a portable urine collection system, according to an embodiment.

Turning now to FIG. 2C, a urine collection system 260 may include a base 267 having a urine volume indicator 265 secured thereto, according to an embodiment. Unless otherwise noted, the urine collection system 260 may include any aspect of other urine collection systems described herein. Although not shown or visible in FIG. 2C, the urine collection system may include any canister, pump, lid, conduit, urine collection device, pressure indicator, and/or flow indicator described herein. Aspects of the urine collection system 260 may be included in other urine collection systems described herein. The pump 116 may be housed in or secured to the base 267 and may be configured to draw air from the interior region of the canister 114.

In some embodiments, the base 267 includes a recess 262 sized to receive at least a portion of the canister 114. For example, at least a portion of the bottom region of the canister 114 may fit within the recess 262 and shaped complementary to the recess 262. The urine volume indicator 265 may include a scale positioned at least partially within the recess 262. The scale may include any scale, gauge, or sensor configured to weigh the canister 114. In some embodiments, the urine volume indicator 265 is positioned the bottom of the recess 262. The volume of the urine in the canister 114 may be determined by a change in weight of the canister 114 before, during, and/or after urine is collected from the user. In some embodiments, the urine volume indicator 265 may be configured to weigh the canister 114 at predetermined intervals, continuously upon activation, and/or continuously for a period of time responsive to detecting a change in weight. The urine volume indicator 265 may be configured to determine the volume of the urine in the canister 114 based on the weight measured by the scale.

In some embodiments, the urine volume indicator 265 includes an ultrasound transducer configured to detect the property relating at least to the volume of the urine in the canister 114. For example, the volume of the urine in the canister 114 may be determined using echo or time of flight of ultrasound waves through the canister 114. In some embodiments, the urine volume indicator 265 is positioned the bottom of the recess 262. In some embodiments, the ultrasound transducer may be positioned or embedded on the canister 114, the lid 119, or on a wall-mounted canister support for a wall-mounted pump or vacuum source.

The urine volume indicator 265 may be configured to transmit data relating to the volume of the urine in the canister 114 as measured by the urine volume indicator 265 to a controller, and the controller may be configured to determine the volume of the urine in the canister 114 based on the data measured by the urine volume indicator 265. In some embodiments, at least one of the urine volume indicator 265 or the controller may be configured to communicate with the alert device 155. For example, at least one of the urine volume indicator 265 or the controller may be configured to communicate with the alert device when the volume of the urine in the canister 114 is at a predetermined level or volume.

Figure 2D:
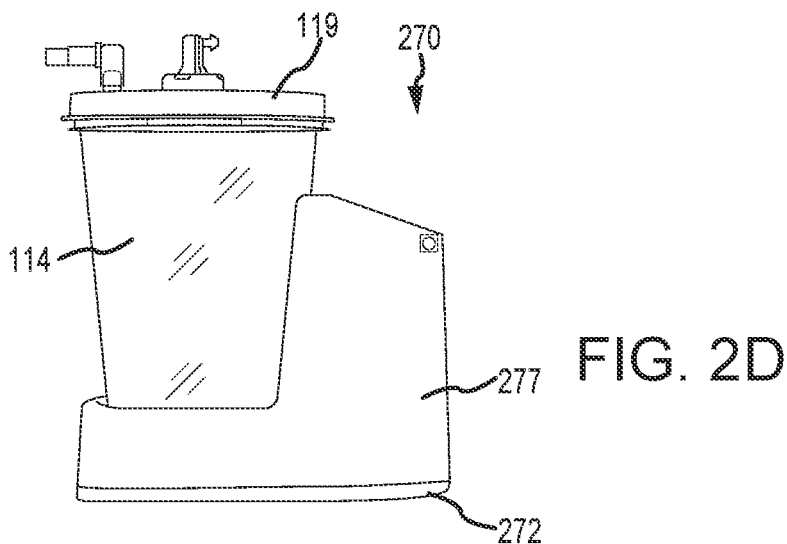
FIG. 2D is a side view of a portable urine collection system, according to an embodiment.

Turning now to FIG. 2D, a urine collection system 270 may include a base 277 that has a urine volume indicator secured thereto, according to an embodiment. Unless otherwise noted, the urine collection system 270 may include any aspect of other urine collection systems described herein. Although not shown or visible in FIG. 2D, the urine collection system may include any pump, conduits, urine collection device, pressure indicator, and/or flow indicator described herein. The pump 116 may be housed in or secured to the base 277 and may be configured to draw air from the interior region of the canister 114.

In some embodiments, the base 277 includes the recess 262 sized to receive at least a portion of the canister 114. For example, at least a portion of the bottom region of the canister 114 may fit within the recess 262 and be complementary to the recess 262. The urine volume indicator may include a scale 272 positioned and/or secured to the base 277. For example, the scale 272 may include one or more (e.g., two, three, four, five, etc.) feet secured to the bottom of the base 277. The scale 272 may include any scale, gauge, or sensor configured to weigh the canister 114 with the base 277. The volume of the urine in the canister 114 may be determined by a change in weight of the canister 114 and the base 277 during or after urine is collected from the user. In some embodiments, the scale 272 may be configured to weigh the canister 114 at predetermined intervals, continuously upon activation, and/or continuously for a period of time responsive to detecting a change in weight. The scale 272 may be configured to determine the volume of the urine in the canister 114 based on the weight measured by the scale 272. In some embodiments, the scale 272 may be configured to transmit data relating to the weight measured by the scale 272 to a controller, and the controller may be configured to determine the volume of the urine in the canister 114 based on the weight measured by the scale 272. In some embodiments, at least one of the scale 272 or the controller may be configured to communicate with the alert device 155. For example, at least one of the scale 272 or the controller may be configured to communicate with the alert device when the volume of the urine in the canister 114 is at a predetermined level or volume.

Figure 2E:
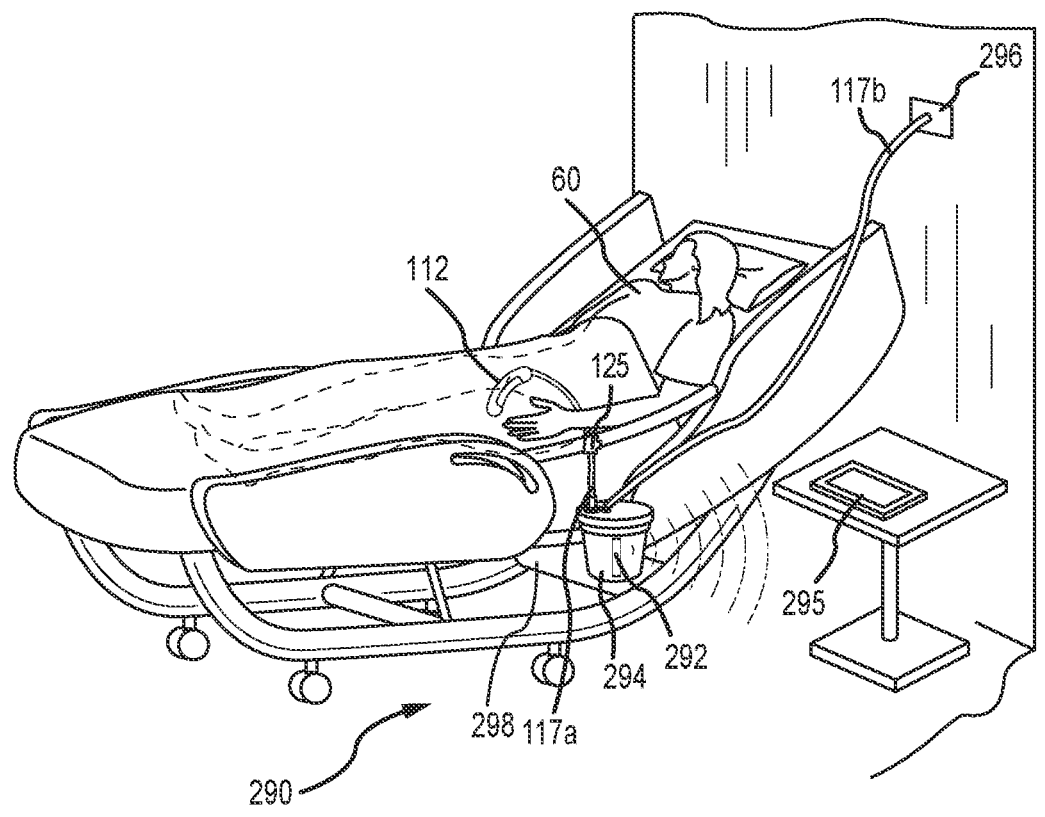
FIG. 2E is a side isometric view of a urine collection system in use, according to an embodiment.

Turning now to FIG. 2E, a urine collection system 290 having a urine volume indicator may be used in a hospital or other care setting, according to an embodiment. Unless otherwise noted, the urine collection system 290 may include any aspect of other urine collection systems described herein. Moreover, aspects of the urine collection system 290 may be applied to any other urine collection system described herein, such as aspects of use in a hospital or care setting. In some settings, the urine collection system 290 may include a wall-mounted pump 296 or vacuum source in fluid communication with the second conduit 117*b* effective create a negative pressure within the canister 294. Aspects of the urine collection system 290, such as the urine volume indicator may be used in settings outside of hospital or care facilities, including home and portable use. As noted above, the urine collection device 112 may be positioned at least proximate to a urethra of the user 60, shown in FIG. 2E.

In some embodiments, the urine volume indicator may include a scale 298 mounted or mountable to a bedframe and configured to support at least the canister 294. In some embodiments, the scale 298 is mounted or mountable to the bedframe and configured to support the canister 114 and the base 107 (not shown), and the wall-mounted vacuum source 296 is absent. In some embodiments, the scale 298 may be mounted or mountable to other objects, such as a wheelchair, a night stand, or a wall. For example, the scale 298 may be mounted on the wall proximate to the wall-mounted vacuum source 296. The scale 298 may include any scale, gauge, or sensor configured to weigh at least the canister 294. The volume of the urine in the canister 294 may be determined by a change in weight of the canister 294 during or after urine is collected from the user 60. In some embodiments, the scale 298 may be configured to weigh the canister 294 at predetermined intervals, continuously upon activation, and/or continuously for a period of time responsive to detecting a change in weight. The scale 298 may be configured to determine the volume of the urine in the canister 294 based on the weight measured by the scale 298.

In some embodiments, the scale 298 may be configured to transmit data relating to the weight measured by the scale 298 to a controller. In some embodiments, the controller includes an external electronic device 295, such as an electronic device having a display monitor that is configured to determine and/or display the volume of urine in the canister 294. In some embodiments, the controller may include a controller housed in the base 107 supporting the canister 294. In some embodiments, at least one of the scale 298 or the controller may be configured to communicate with the alert device on the electronic device 295, in the room, at an aid station, or other electronic device. For example, at least one of the scale 298 or the controller may be configured to communicate with an alert device when the volume of the urine in the canister 294 is at a predetermined level or volume.

The urine volume indicator of the urine collection system 290 may include a sensor 292 secured to or embedded in at least one the canister 294 or the lid and configured to detect the property relating at least to the volume of the urine in the canister 294. The urine collection system 290 may include the sensor 292 in addition to the scale 298 or in alternative to the scale 298 (e.g., the scale is absent). In some embodiments, the urine collection system 290 includes the scale 298, and the sensor 292 is absent (e.g., the urine collection system 290 includes the canister 114). The sensor 292 may include at least one of a conductive, impedance, or radio-frequency identification (RFID) sensor that is configured to detect the property relating at least to the volume of the urine in the canister 294. The sensor 292 also may be configured to wirelessly communicate with the external electronic device 295. The external electronic device 295 may be configured to use the data received from the sensor 292 to determine the volume of the urine in the canister 294. In some embodiments, the external electronic device may be configured to produce an alert signal when the volume of the urine in the canister 294 is at or surpassing a predetermined volume. In some embodiments, the external electronic device 295 may be configured to transmit an alert message to one or more other electronic devices indicating that the volume of the urine in the canister is at or surpassing the predetermined volume.

Returning now to FIG. 1B, the urine collection system 100 may include the flow indicator 125 to allow a user or caregiver to confirm that air or fluid is flowing in the urine collection system 100. The flow indicator 125 may be positioned between the canister 114 and the urine collection device 112 and configured to detect a property relating at least to a flow of fluid through the first conduit 117*a*. In some embodiments, the flow indicator 125 may be positioned in-line with the first conduit 117*a* to indicate fluid and/or air are flowing through the first conduit 117*a*. The flow indicator 125 may be positioned in-line between the canister 114 and the urine collection device 112, and may be configured to detect a property relating at least to a flow of fluid through the first conduit 117*a*. In some embodiments, an additional flow indicator may be similarly secured or positioned on the second conduit 117*b* to detect a property relating at least to a flow of air through the second conduit 117*b*.

The flow indicator 125 may utilize the motion of air or fluid in the first conduit 117*a* to provide a visual or audible indication of the motion or flow of air or fluid in the first conduit 117*a*. In some embodiments, the flow indicator 125 includes an enclosed wheel that spins or rotates responsive to fluid flow through the indicator 125. Thus, a user or caregiver can quickly view the flow indicator and determine if air or liquid is flowing through the first conduit 117*a* by whether or not the enclosed wheel is spinning or rotating. If the pump 116 is activated and the enclosed wheel of the flow indicator is not spinning or rotating, at least one of the first conduit 117*a* or the second conduit 117*b* may be kinked (e.g., have a sharp twist, bend, or curve that inhibits or prevents the flow of fluid through the respective conduit), and/or the canister 114 may not be sealed. When one of the first conduit 117*a* or the second conduit 117*b* are kinked and/or the canister 114 is not sealed, urine voided into the urine collection device 112 may not be drawn into the canister 114, and may instead overflow from the urine collection device 112. Thus, the flow indicator 125 in at least one, some, or all embodiments prevent undesired and unhygienic displacement of urine on or around the user.

Turning ahead in the drawings to FIG. 3, in some embodiments, a flow indicator 300 may replace the flow indicator 125. The flow indicator 300 may be configured to detect a property relating at least to a flow of fluid through the first conduit 117a. In some embodiments, the flow indicator 300 includes a tube 302 and a float 310 or ball movable in the tube 302 responsive to fluid flow through the flow indicator 300. For example, the float 310 may be at a first position in the tube 302 when no fluid flow is present. The float 310 may raise or lower within the tube 302 when fluid flow is present. In some embodiments, the tube 305 includes one or more markers 305 positioned on the tube 302 to indicate a predetermined fluid flow is present in the first conduit 117a when the float 310 reaches the one or more markers 305. In some embodiments, the one or more markers 305 each indicate a flow rate of fluid through the flow indicator 300. The flow indicator 300 also may include a gauge 306 having a needle and a numeric and/or colored scale indicating a rate or relative rate of flow fluid through the flow indicator 300. For example, the needle in the gauge 306 may move responsive to fluid flow to a number indicating the approximate rate of fluid flow through the flow indicator 300. In some embodiments, the needle in the gauge 306 may move to a color (e.g., red, yellow, or green) indicating an acceptable or unacceptable rate of fluid flow through the fluid indicator 300.

In some embodiments of the fluid collection system 100, fluid indicator 125, 300 may be configured to communicate with the alert device 155, and the alert device 155 may be configured to produce an alert signal when the pump 116 is activated but the flow indicator 125, 300 indicates that no fluid flow is present or the fluid flow is below a predetermined level. The alert signal produced responsive to the flow indicator 125, 300 may include at least one of a visual (e.g., light) alert, an audible (e.g., sound) alert, or a haptic alert. In some embodiments, the visual alert or the audible alert associated with the flow indicator 125, 300 may be different than the visual alert or the audible alert produced responsive to the urine volume indicator 135. The flow indicator 125, 300 may be wired or wirelessly coupled to the pump 116 in the urine collection system 100 effective to deactivate (e.g., turn off) the pump when the pump 116 is activated and the flow indicator 125, 300 indicates no fluid flow is present in the first conduit 117a. The urine collection system 100 also may include a controller configured to facilitate communication between the flow indicator 125, 300 and at least one (e.g., both) of the pump 116 and the alert device 155.

Returning to FIG. 1B, the urine collection system 100 may include a pressure indicator 115 secured to or positioned on the canister 114 or the lid 119 and configured to detect a property relating at least to a pressure in the interior region of the canister 114. During use of the urine collection system 100, a user or caregiver may desire to confirm that there is pressure in the canister 114 of the urine collection system 100. If the desired negative pressure is absent from the canister 114 while the pump 116 is activated, urine may not be drawn from the urine collection device 112 as desired, resulting in urine overflowing from the urine collection device 112 as urine is voided by the user. In some embodiments, the pressure sensor 115 may include an electric pressure sensor positioned within the canister 114, such as secured to an interior surface of the canister 114 or the lid 119.

Turning ahead in the drawings to FIGS. 4A and 4B, in some embodiments, the pressure indicator 115 includes a button 400 positioned on the lid 119 or the canister 114. The button 400 may be configured to extend outward (shown in FIG. 4B) when a negative pressure is absent in the interior region of the canister 114, e.g., the pump 116 is not activated. The button 400 also may be configured to extend inward (shown in FIG. 4A) when the negative pressure is present in the interior region of the canister 114, e.g., the pump 116 is activated. A user or caregiver, then, can view the pressure indicator 115 and quickly determine if the desired negative pressure is present in the interior region of the canister 114 while the pump 116 is activated. If, for example, the pump 116 is activate but the button 400 remains extended outward, the second conduit 117b may be kinked or the canister 114 may not be properly sealed.

In some embodiments of the fluid collection system 100, pressure indicator 115 may be configured to communicate with alert device 155, and the alert device 155 may be configured to produce an alert signal when the pump 116 is activated but the pressure indicator 115 indicates that a negative pressure is absent from the interior region of the canister 114. The alert signal produced responsive to the pressure indicator 115 may include at least one of a visual (e.g., light) alert, an audible (e.g., sound) alert, or a haptic alert. In some embodiments, the visual alert or the audible alert associated with the pressure indicator 115 may be different than the visual alert or the audible alert produced responsive to the urine volume indicator 135 and/or the flow indicator 125. The pressure indicator 115 may be wired or wirelessly coupled to the pump 116 in the urine collection system 100 effective to activate (e.g., turn off) the pump when the pump 116 is activated and the pressure indicator 115 indicates that a negative pressure is absent from the interior region of the canister 114. The urine collection system 100 also may include a controller configured to facilitate communication between the pressure indicator 115 and at least one (e.g., both) of the pump 116 and the alert device 155.

Figure 5:
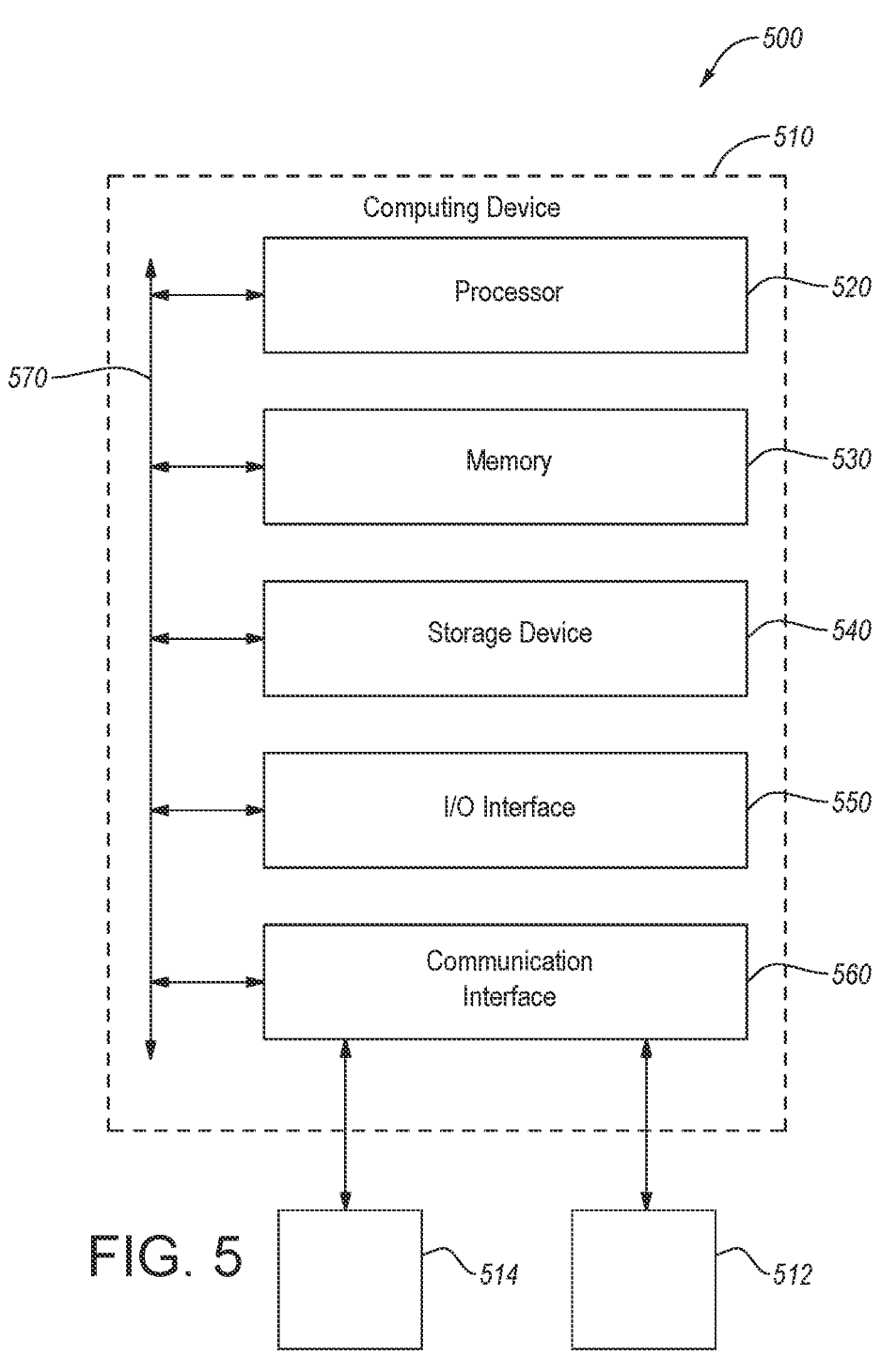
FIG. 5 is a block diagram of a controller, according to an embodiment.

As noted above, the urine collection systems described herein may include a controller that may be configured to communicate with one or more (e.g., all) of the alert device 155, the pressure indicator 115, the flow indicator 125, 300, and/or the urine volume indicator 135, 235, 265, 272, 285, 292, 298. FIG. 5 is a schematic of a controller 500 that may be included in any of the urine collection systems described herein. For example, the controller may be housed in or secured to the base of the urine collection system, and/or may be included in one or more (e.g., all) of the alert device 155, the pressure indicator 115, the flow indicator 125, 300, and/or the urine volume indicator 135, 235, 265, 272, 285, 292, 298.

The controller 500 includes at least one computing device 510. The at least one computing device 510 is an exemplary computing device that may be configured to perform one or more of the acts described herein. The at least one computing device 510 can include one or more servers, one or more computers (e.g., desk-top computer, lap-top computer), or one or more mobile computing devices (e.g., smartphone, tablet, etc.). The computing device 510 can comprise at least one processor 520, memory 530, a storage device 540, an input/output ("I/O") device/interface 550, and a communication interface 560. While an example computing device 510 is shown in FIG. 5, the components illustrated in FIG.

5 are not intended to be limiting of the controller 500 or computing device 510. Additional or alternative components may be used in some examples. Further, in some examples, the controller 500 or the computing device 510 can include fewer components than those shown in FIG. 5. For example, the controller 500 may not include the one or more additional computing devices 512, 514. In some examples, the at least one computing device 510 may include a plurality of computing devices, such as a server farm, computational network, or cluster of computing devices. Components of computing device 510 shown in FIG. 5 are described in additional detail below.

In some examples, the processor(s) 520 includes hardware for executing instructions (e.g., instructions for carrying out one or more portions of any of the methods disclosed herein), such as those making up a computer program. For example, to execute instructions, the processor(s) 520 may retrieve (or fetch) the instructions from an internal register, an internal cache, the memory 530, or a storage device 540 and decode and execute them. As an example, the processor(s) 520 may include one or more instruction caches, one or more data caches, and one or more translation lookaside buffers (TLBs). Instructions in the instruction caches may be copies of instructions in memory 530 or storage device 540. In some examples, the processor 520 may be configured (e.g., include programming stored thereon or executed thereby) to carry out one or more portions of any of the example methods disclosed herein.

In some examples, the processor 520 is configured to perform any of the acts described herein and/or cause one or more portions of the computing device 510 or controller 500 to perform at least one of the acts disclosed herein. Such configuration can include one or more operational programs (e.g., computer program products) that are executable by the at least one processor 520. For example, the processor 520 may be configured to automatically communicate with the alert device 155 and/or communicate with the pump to activate or deactivate the pump.

The at least one computing device 510 (e.g., a server) may include at least one memory storage medium (e.g., memory 530 and/or storage device 540). The computing device 510 may include memory 530, which is operably coupled to the processor(s) 520. The memory 530 may be used for storing data, metadata, and programs for execution by the processor(s) 520. The memory 530 may include one or more of volatile and non-volatile memories, such as Random Access Memory (RAM), Read Only Memory (ROM), a solid state disk (SSD), Flash, Phase Change Memory (PCM), or other types of data storage. The memory 530 may be internal or distributed memory.

The computing device 510 may include the storage device 540 having storage for storing data or instructions. The storage device 540 may be operably coupled to the at least one processor 520. In some examples, the storage device 540 can comprise a non-transitory memory storage medium, such as any of those described above. The storage device 540 (e.g., non-transitory storage medium) may include a hard disk drive (HDD), a floppy disk drive, flash memory, an optical disc, a magneto-optical disc, magnetic tape, or a Universal Serial Bus (USB) drive or a combination of two or more of these. Storage device 540 may include removable or non-removable (or fixed) media. Storage device 540 may be internal or external to the computing device 510. In some examples, storage device 540 may include non-volatile, solid-state memory. In some examples, storage device 540 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these. In some examples, one or more portions of the memory 530 and/or storage device 540 (e.g., memory storage medium(s)) may store one or more databases thereon.

In some examples, one or more of urine collection history, pump history, or alert history may be stored in a memory storage medium such as one or more of the at least one processor 520 (e.g., internal cache of the processor), memory 530, or the storage device 540. In some examples, the at least one processor 520 may be configured to access (e.g., via bus 570) the memory storage medium(s) such as one or more of the memory 530 or the storage device 540. For example, the at least one processor 520 may receive and store the data (e.g., look-up tables) as a plurality of data points in the memory storage medium(s). The at least one processor 520 may execute programming stored therein adapted access the data in the memory storage medium(s).

The computing device 510 also includes one or more I/O devices/interfaces 550, which are provided to allow a user to provide input to, receive output from, and otherwise transfer data to and from the computing device 510. These I/O devices/interfaces 550 may include a mouse, keypad or a keyboard, a touch screen, camera, optical scanner, network interface, web-based access, modem, a port, other known I/O devices or a combination of such I/O devices/interfaces 550. The touch screen may be activated with a stylus or a finger.

The I/O devices/interfaces 550 may include one or more devices for presenting output to a user, including, but not limited to, a graphics engine, a display (e.g., a display screen or monitor), one or more output drivers (e.g., display drivers), one or more audio speakers, and one or more audio drivers. In certain examples, I/O devices/interfaces 550 are configured to provide graphical data to a display for presentation to a user. The graphical data may be representative of one or more graphical user interfaces and/or any other graphical content as may serve a particular implementation.

The computing device 510 can further include a communication interface 560. The communication interface 560 can include hardware, software, or both. The communication interface 560 can provide one or more interfaces for communication (such as, for example, packet-based communication) between the computing device 510 and one or more additional computing devices 512, 514 or one or more networks. The one or more additional computing devices, for example, may include any of the indicators described herein or external electronic devices. The one or more additional computing devices may include any aspect of the controller 500 described herein. For example, communication interface 560 may include a network interface controller (NIC) or network adapter for communicating with an Ethernet or other wire-based network or a wireless NIC (WNIC) or wireless adapter for communicating with a wireless network, such as a WI-FI.

Any suitable network and any suitable communication interface 560 may be used. For example, computing device 510 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, one or more portions of controller 500 or computing device 510 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof. Computing device 510 may include any suitable communication interface 560 for any of these networks, where appropriate.

The computing device 510 may include a bus 570. The bus 570 can include hardware, software, or both that couples components of computing device 510 to each other. For example, bus 570 may include an Accelerated Graphics Port (AGP) or other graphics bus, an Enhanced Industry Standard Architecture (EISA) bus, a front-side bus (FSB), a HYPER-TRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

FIG. 6 is a flow diagram of a method 600 of collecting urine from a user, according to an embodiment. The method 600 includes an act 610 positioning a fluid collection device at least proximate to a urethra of a user. The fluid collection device may be in fluid communication with an interior region of a canister through a first conduit. The method 600 includes an act 620 of activating a pump in fluid communication with the interior region of the canister through a second conduit effective to create a negative pressure in the canister and draw urine from the urine collection device through the first conduit into the interior region of the canister. The method 600 includes an act 630 of monitoring at least one property of the urine collection system with one or more indicators.

In some embodiments, the act 630 includes monitoring at least a property relating at least to a volume of urine in the canister with a urine volume indicator secured to the canister. In these and other embodiments, the method 600 may include an act of deactivating the pump when the urine volume indicator indicates the volume of the urine in the canister has reached a predetermined volume.

In some embodiments, the act 630 includes monitoring at least a property relating at least to a flow of fluid through the first conduit with a flow indicator in fluid communication with the first conduit and positioned between the canister and the urine collection device. In these and other embodiments, the method 600 may include an act of removing a kink in the first conduit when the fluid indicator indicates the flow of the fluid through the first conduit is absent or below a predetermined rate after the pump has been activated.

In some embodiments, the act 630 includes monitoring at least a property relating at least to a pressure in the interior region of the canister with a pressure indicator secured to the canister. In these and other embodiments, the method 600 may include at least one act of sealing a lid on the canister or removing a kink in the second conduit when the pressure indicator indicates an absence of negative pressure in the interior region of the canister after the pump has been activated.

The acts of the method 600 described above are for illustrative purposes. For example, the acts of the method 600 can be performed in different orders, split into multiple acts, modified, supplemented, or combined. In an embodiment, one or more of the act of the method 600 can be omitted from the method 600. Any of the acts of the method 600 can include using any of the urine collection systems disclosed herein.

As used herein, the term "about" or "substantially" refers to an allowable variance of the term modified by "about" or "substantially" by ±10% or ±5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:

1. A urine collection system, comprising:
a urine collection device configured to be positioned at least proximate to a urethra of a user;
a canister having a sidewall defining an interior region;
a first conduit in fluid communication with the urine collection device and the canister;
a pressure indicator secured to the canister and configured to detect a property relating at least to a pressure in the interior region of the canister, wherein the pressure indicator includes a button positioned on the sidewall of the canister such that the pressure indicator is visible during use of the urine collection system, the button configured to extend outward when a negative pressure is absent in the interior region and configured to extend inward when the negative pressure is present in the interior region;
a urine volume indicator configured to detect a property relating at least to a volume of urine in the canister, wherein the urine volume indicator includes a float member configured to float on the urine in the canister;
a lid secured or securable to the canister, wherein the urine volume indicator further includes:
a body secured to an inner surface of the lid or an inner surface of the sidewall of the canister;
a wheel or dial forming at least a semi-circle pivotably secured to the body to pivot about an axis and including colors representing percent capacity of the canister; and
an arm connecting the float member to the wheel,
wherein the wheel or dial rotates responsive to movement of the float member to expose a color of the colors representing the percent capacity of the canister.

2. The urine collection system of claim 1, further comprising:
a support member secured to at least one of the canister or the lid; and
a marker movable on the support member responsive to vertical movement of the float member to indicate at least a relative amount of the urine in the canister.

3. The urine collection system of claim 2, further comprising an alert device in communication with the urine volume indicator and configured to produce an alert signal when the relative amount of the urine in the canister is at a predetermined volume.

4. The urine collection system of claim 1, further comprising a scale configured to determine the property of a weight related to the volume of the urine in the canister.

5. The urine collection system of claim 4, wherein the scale is configured to weigh the canister continuously or at predetermined intervals.

6. The urine collection system of claim 4, further comprising a base including a pump or vacuum source configured to draw air from the interior region of the canister and a recess sized to receive at least a portion of the canister, wherein the scale is secured to the base.

7. The urine collection system of claim 6, wherein the scale is positioned in the recess in the base.

8. The urine collection system of claim 6, where the scale includes one or more feet secured to the base.

9. The urine collection system of claim 6, wherein at least one of the scale or a controller in communication with the scale and positioned in the base is configured to determine the volume of the urine in the canister based on the weight of the canister.

10. The urine collection system of claim 9, further comprising an alert device in communication with at least one of the scale or the controller and configured to produce an alert signal when the volume of the urine in the canister is at a predetermined volume.

11. The urine collection system of claim 4, wherein the scale configured to is configured to be secured to a bed frame or a wall and support at least the canister.

12. The urine collection system of claim 11, further comprising a base including a pump or vacuum source configured to draw air from the interior region of the canister and a recess sized to receive at least a portion of the canister, wherein the scale is configured to support the base and the canister positioned in the recess.

13. The urine collection system of claim 1, further comprising an ultrasound transducer configured to detect the property relating at least to the volume of the urine in the canister.

14. The urine collection system of claim 13, further comprising a base including a pump or vacuum source configured to draw air from the interior region of the canister and a recess sized to receive at least a portion of the canister, wherein the ultrasound transducer is positioned in the recess.

15. The urine collection system of claim 13, wherein the ultrasound transducer is secured or securable to at least one of the canister or the lid secured to the canister.

16. The urine collection system of claim 1, further comprising a sensor secured to or embedded in the canister and configured to detect the property relating at least to the volume of the urine in the canister and wirelessly communicate with an electronic device.

17. The urine collection system of claim 16, wherein the sensor includes an impedance sensor.

18. The urine collection system of claim 16, wherein the electronic device is configured to produce an alert signal when the volume of the urine in the canister is at a predetermined volume.

19. The urine collection system of claim 1, further comprising a flow indicator positioned to detect a property relating at least to a flow of fluid through the first conduit between the canister and the urine collection device.

20. The urine collection system of claim 19, wherein the flow indicator includes an enclosed wheel that rotates responsive to fluid flow through the flow indicator and provides an audible indication of the fluid flow through the flow indicator.

21. The urine collection system of claim 19, wherein the flow indicator includes a tube and a float movable in the tube responsive to fluid flow through the flow indicator.

22. The urine collection system of claim 21, wherein the tube includes a marker positioned on the tube to indicate a predetermined fluid flow when the float reaches the marker.

23. The urine collection system of claim 20, further comprising an alert device in communication with the flow indicator and configured to produce an alert signal when the fluid flow is disrupted.

24. The urine collection system of claim 1, further comprising an alert device in communication with the pressure and configured to produce an alert signal when the negative pressure in the interior region begins and/or ends.

25. The urine collection system of claim 1, further comprising a pump in fluid communication with the canister and configured to create a negative pressure on the interior region of the canister effective to draw urine from the urine collection device through the first conduit into the canister.

26. A method of collecting urine from a user, the method comprising:
    positioning a fluid collection device at least proximate to a urethra of a user, the fluid collection device being in fluid communication with an interior region of a canister through a first conduit;
    activating a pump in fluid communication with the interior region of the canister effective to create a negative pressure in the canister and draw urine from the urine collection device through the first conduit into the interior region of the canister;
    visually monitoring a property relating at least to a pressure in the interior region of the canister with a pressure indicator secured to a sidewall of the canister, wherein the pressure indicator includes a button positioned on the sidewall of the canister, the button configured to extend outward when a negative pressure is absent in the interior region and configured to extend inward when the negative pressure is present in the interior region; and
    monitoring a property relating at least to the volume of urine in the canister with the urine volume indicator, the urine volume indicate including a body secured to an inner surface of the lid or an inner surface of the sidewall of the canister, a wheel or dial forming at least a semi-circle pivotably secured to the body to pivot about an axis and including colors representing percent capacity of the canister, and an arm connecting the float member to the wheel, wherein monitoring the property relating at least to the volume of the urine in the canister with the urine volume indicator includes monitoring the wheel or the dial rotating responsive to movement of the float member to expose a color of the colors representing the percent capacity of the canister.

27. The method of claim 26, further comprising deactivating the pump when the urine volume indicator indicates the volume of the urine in the canister has reached a predetermined volume.

28. The method of claim 26, further comprising monitoring a property relating at least to the flow of fluid through the first conduit with the flow indicator in fluid communication with the first conduit and positioned between the canister and the urine collection device.

29. The method of claim 28, further comprising removing a kink in the first conduit when the fluid indicator indicates the flow of the fluid through the first conduit is absent or below a predetermined rate after the pump has been activated.

30. The method of claim 26, further comprising at least one of sealing the lid on the canister or removing a kink in the second conduit when the button on the sidewall of the canister extends outward and indicates an absence of nega-
tive pressure in the interior region of the canister after the
pump has been activated.

* * * * *

20